(12) United States Patent
Umezu et al.

(10) Patent No.: US 7,232,592 B2
(45) Date of Patent: Jun. 19, 2007

(54) NEMATIC LIQUID CRYSTAL COMPOSITION CONTAINING INDANE COMPOUND

(75) Inventors: Yasuo Umezu, Kitamoto (JP); Shotaro Kawakami, Oosato-gun (JP); Kiyofumi Takeuchi, Tokyo (JP); Tetsuo Kusumoto, Ageo (JP); Shinji Ogawa, Saitama (JP)

(73) Assignee: Dainippon Ink and Chemicals, Inc., Tokyo (JP)

( * ) Notice: Subject to any disclaimer, the term of this patent is extended or adjusted under 35 U.S.C. 154(b) by 22 days.

(21) Appl. No.: 10/536,421

(22) PCT Filed: Nov. 27, 2003

(86) PCT No.: PCT/JP03/15181

§ 371 (c)(1),
(2), (4) Date: May 26, 2005

(87) PCT Pub. No.: WO2004/050797

PCT Pub. Date: Jun. 17, 2004

(65) Prior Publication Data

US 2006/0102878 A1     May 18, 2006

(30) Foreign Application Priority Data

Nov. 29, 2002   (JP)   ............. 2002-347615

(51) Int. Cl.
C09K 19/32 (2006.01)
C09K 19/30 (2006.01)
C07C 25/22 (2006.01)

(52) U.S. Cl. ............. 428/1.1; 252/299.62; 252/299.63; 570/183; 570/187

(58) Field of Classification Search ........... 252/299.01, 252/299.5, 299.61, 299.62, 299.63; 428/1.1; 570/183, 187
See application file for complete search history.

(56) References Cited

U.S. PATENT DOCUMENTS 6,485,797 B1   11/2002   Schmidt et al.

FOREIGN PATENT DOCUMENTS

| DE | 19840447 | 3/2000 |
|---|---|---|
| EP | 0 637 585 A1 | 2/1995 |
| JP | 6-263663 | 9/1994 |
| JP | 7-70060 | 3/1995 |
| JP | 2001-11450 | 1/2001 |
| JP | 2001-164252 | 6/2001 |
| JP | 2001-520256 | 10/2001 |
| WO | 94/18285 A1 | 8/1994 |
| WO | 99/19420 A2 | 4/1999 |

OTHER PUBLICATIONS

English translation by computer for JP 2001-164252, http://www4.ipdl.ncipi.go.jp/Tokujitu/PAJdetail.ipdl?N0000=60&N0120=01&N2001=2&N3001=2001-164252.*

European Search Report dated Dec. 22, 2005.

* cited by examiner

*Primary Examiner*—Shean C. Wu
(74) *Attorney, Agent, or Firm*—Armstrong, Kratz, Quintos, Hanson & Brooks, LLP

(57) ABSTRACT

The present invention provides a nematic liquid crystal composition using a 4,6-difluoroindane-based compound that has a low lower limit temperature ($T_{\rightarrow N}$) of the liquid crystal phase, high upper limit temperature ($T_{N-I}$) of the liquid crystal phase, and wide liquid crystal phase temperature range without impairing response speed, threshold voltage and other liquid crystal characteristics within a the range of the optimal Δn as a nematic liquid crystal, and a 4,6-difluoroindane-based compound that is used in said liquid crystal composition.

The nematic liquid crystal composition contains at least one type of compound having a 4,6-difluoroindan-2,5-diyl group, and the refractive index anisotropy is within the range of 0.08 to 0.15, the liquid crystal phase upper limit temperature is 70° C. or higher, the liquid crystal phase lower limit temperature is −20° C. or lower, and the difference between the liquid crystal phase upper limit temperature and liquid crystal phase lower limit temperature is 90° C. or more.

20 Claims, No Drawings

NEMATIC LIQUID CRYSTAL COMPOSITION CONTAINING INDANE COMPOUND

TECHNICAL FIELD

The present invention relates to a nematic liquid crystal composition that is useful as an electrooptical liquid crystal display, a liquid crystal display element that uses said composition, and an indane-based compound that is useful as a composite material of a nematic liquid crystal composition.

BACKGROUND ART

In liquid crystal display elements including twist nematic, super twist nematic and active matrix liquid crystal display elements, and particularly medium- and small-size portable liquid crystal display elements, the stability of the display with respect to the temperature of the usage environment is an important factor, and liquid crystal materials are being required to have lower drive voltages enabling reductions in response and power consumption, or lower drive voltages in temperature ranges of −30° C. to 0° C. or 40° C. to 80° C., reduced sharpness and smaller frequency dependency of duty cycle driving.

In particular, the liquid crystal phase temperature range ($\Delta T$), which is the absolute value of the difference between the lower limit temperature ($T_{\rightarrow N}$) of the liquid crystal phase and the upper limit temperature ($T_{N-I}$) of the liquid crystal phase, is important due to increased outdoor use to take advantage of the lower power consumption characteristics of liquid crystal elements. However, in the case of combining conventional materials, although it is possible to increase the liquid crystal phase temperature range, since accompanying increases in threshold voltage, increases in response speed and anisotropy of the refractive index ($\Delta n$) occur that are outside the optimum range of a nematic liquid crystal, a sufficient liquid crystal phase temperature range is unable to be obtained (pamphlet of International Publication WO 00/17287, Japanese Unexamined Patent Application, First Publication No. 2001-11450 (p. 6)). Consequently, there is a need to develop a liquid crystal composition having a wide liquid crystal phase temperature range, and a liquid crystal material optimum for outdoor use, without impairing the response speed and various other characteristics of the liquid crystal.

On the other hand, liquid crystal compounds having indane in their backbone are already known, and several of these compounds have been disclosed. However, liquid crystal compositions using these previously disclosed indane derivatives have the problems described below. For example, although a compound having a 5,6-difluoroindan-2-yl group (pamphlet of International Publication WO94/18285 (pp. 27–29), Japanese Unexamined Patent Application, First Publication No. H6-263663 (pp. 9–10)) has the characteristics of a rapid response speed despite having a comparatively large $\Delta\epsilon$, the lower limit temperature of the liquid crystal phase is quite low, thereby delaying its application as a practical nematic liquid crystal composition.

In addition, inventions have also been disclosed that comprehensively include a compound having a 4,6-difluoroindan-2,5-diyl group (European Unexamined Patent Publication No. 637585 (p. 31 to Examples), Japanese Unexamined Patent Application, First Publication No. H7-70060 (p. 30 to Examples). However, these cited references do not provide specific disclosures of the production process and physical property values of a compound having fluorine atoms at positions 4 and 6 of an indane ring. Although these cited references describe that the compound can be used as a nematic liquid crystal composition, what type of compound is combined with this compound to compose of nematic liquid crystal composition, and what characteristics are demonstrated in the case of using this liquid crystal composition are not disclosed. In addition, liquid crystal compositions using this liquid crystal composition are also already known, and examples of preferable compounds have been disclosed (pamphlet of International Publication WO 99/19420 (pp. 30–35)). However, the compound disclosed here does not have fluorine atoms at positions 4 and 6 of an indane ring, but rather has a special cyclic structure or acyclic structure consisting primarily of a substituent at position 2. Moreover, the liquid crystal composition disclosed here is a liquid crystal composition used in a ferroelectric liquid crystal element, there is no disclosure relating to a nematic liquid crystal composition.

On the basis of the above, a compound having fluorine atoms at positions 4 and 6 of an indane ring, and a nematic liquid crystal composition in which said compound is applied are not known, and there is a need to develop a nematic liquid crystal composition using a compound having a 4,6-difluoroindan-2,5-diyl group that has a wide liquid crystal phase temperature range and superior characteristics.

DISCLOSURE OF THE INVENTION

The object of the present invention is to provide a nematic liquid crystal composition using a compound having a 4,6-difluoroindan-2,5-diyl group that has a low lower limit temperature ($T_{\rightarrow N}$) of the liquid crystal phase, high upper limit temperature ($T_{N-I}$) of the liquid crystal phase, and wide liquid crystal phase temperature range without impairing response speed, threshold voltage and other liquid crystal characteristics within a the range of the optimal $\Delta n$ as a nematic liquid crystal, as well as provide a compound having a 4,6-difluoroindan-2,5-diyl group used in said liquid crystal composition.

The inventors of the present invention completed the present invention as a result of examining nematic liquid crystal compositions containing a 4,6-difluoroindane compound in order to solve the aforementioned problems.

Namely, the present invention provides a nematic liquid crystal composition containing one or more types of a compound having a 4,6-difluoroindan-2,5-diyl group in its backbone, having refractive index anisotropy within the range of 0.08 to 0.15, having a liquid crystal phase upper limit temperature of 70° C. or higher, having a liquid crystal phase lower limit temperature of −20° C. or lower, and having a difference between the liquid crystal phase upper limit temperature and liquid crystal phase lower limit temperature of 90° C. or more, while also providing a liquid crystal element that uses said nematic liquid crystal composition as a composite material.

The present invention also provides a 4,6-difluoroindane-based compound used in said liquid crystal composition that is represented by general formula (Ib):

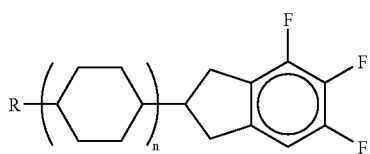

(wherein, R represents an alkyl group having 1 to 12 carbon atoms or an alkenyl group having 2 to 12 carbon atoms, and n represents an integer of 1 or 2).

BEST MODE FOR CARRYING OUT THE INVENTION

The following provides an explanation of an example of the present invention.

Although the present invention contains at least one type of compound having a 4,6-difluoroindan-2,5-diyl group, it preferably contains one to six types of said compound, more preferably one to four types, and particularly preferably one to three types. If the total content of said compound is excessively high, response speed worsens, while if the total content is excessively low, the threshold voltage increases. Thus, the total content of said compound is preferably within the range of 5 to 50% by weight, and particularly preferably within the range of 10 to 40% by weight.

A compound having a 4,6-difluoroindan-2,5-diyl group in the nematic liquid crystal composition of the present invention is preferably a compound represented by general formula (I):

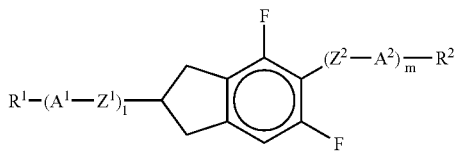

(wherein, $R^1$ represents an alkyl group having 1 to 15 carbon atoms, an alkenyl group having 2 to 15 carbon atoms, or a hydrogen atom, said alkyl group or alkenyl group may be non-substituted or have one or more fluorine atoms, chlorine atoms, methyl groups or trifluoromethyl groups as substituents, one or more methylene groups present in said alkyl group or alkenyl group may be substituted with —CO— or may be substituted with —S—, —O—, —OCOO—, —OCO— or —COO— in which the oxygen atoms are not mutually and directly bonded;

$A^1$ and $A^2$ respectively and independently represent a group selected from the group consisting of:

(a1) a trans-1,4-cyclohexylene group (wherein one methylene group or two or more non-adjacent methylene groups present in this group may be substituted with —O— or —S—), (b1) a 1,4-phenylene group (wherein one —CH= or two non-adjacent —CH= present in this group may be substituted with a nitrogen atom), and (c1) a 1,4-cyclohexenylene group, 1,4-bicyclo(2.2.2)octylene group, piperidin-1,4-diyl group, naphthalen-2,6-diyl group, decahydronaphthalen-2,6-diyl group and 1,2,3,4-tetrahydronaphthalen-2,6-diyl group, and the groups of (a1), (b1) or (c1) may each be substituted with a cyano group, fluorine atom or chlorine atom;

l and m respectively and independently represent 0, 1 or 2, and the sum of l and m is 2 or less;

$Z^1$ and $Z^2$ respectively and independently represent a group selected from the group consisting of —COO—, —OCO—, —CH$_2$O—, —OCH$_2$—, —CH$_2$CH$_2$—, —CH=CH—, —C≡C—, —(CH$_2$)$_4$—, —CH=CH—CH$_2$CH$_2$—, —CH$_2$CH$_2$—CH=CH— and a single bond;

$R^2$ represents a hydrogen atom, fluorine atom, chlorine atom, cyano group, trifluoromethyl group, fluoromethoxy group, difluoromethoxy group, trifluoromethoxy group, 2,2,2-trifluoroethyl group, alkyl group having 1 to 15 carbon atoms, alkenyl group having 2 to 15 carbon atoms or a hydrogen atom, said alkyl group or alkenyl group may be non-substituted or have one or more fluorine atoms, chlorine atoms, methyl groups or trifluoromethyl groups as substituents, and one or more methylene groups present in said alkyl group or alkenyl group may be substituted with —CO— or may be substituted with —S—, —O—, —OCOO—, —OCO— or —COO— in which the oxygen atoms are not mutually and directly bonded; and, in the case a plurality of $A^1$, $A^2$, $Z^1$ and $Z^2$ are present, they may be the same or different).

In general formula (I), since it becomes difficult to express a nematic phase if the side chain is excessively long, $R^1$ preferably represents an alkyl group having 1 to 10 carbon atoms or an alkenyl group having 2 to 10 carbon atoms, more preferably a non-substituted alkyl group having 1 to 8 carbon atoms or non-substituted alkenyl group having 2 to 8 carbon atoms, and even more preferably a structure represented by the following formulas (a) to (e) in the case of representing an alkenyl group:

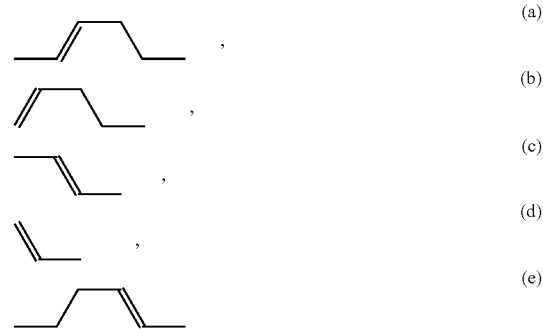

(wherein, each of these structural formulas is linked to $A^1$ or indane ring on the right side).

$A^1$ preferably represents a trans-1,4-cyclohexylene group, 1,4-phenylene group, 3-fluoro-1,4-phenylene group or 3,5-difluoro-1,4-phenylene group, and more preferably a 1,4-phenylene group or trans-1,4-cyclohexylene group.

$A^2$ preferably represents a trans-1,4-cyclohexylene group, 1,4-phenylene group, 3-fluoro-1,4-phenylene group or 3,5-difluoro-1,4-phenylene group, and more preferably a 1,4-phenylene group, 3-fluoro-1,4-phenylene group or 3,5-difluoro-1,4-phenylene group.

$Z^1$ and $Z^2$ respectively and independently preferably represent —COO—, —OCO—, —CH$_2$CH$_2$—, —C≡C—, —(CH$_2$)$_4$— or a single bond, more preferably —CH$_2$CH$_2$—, —C≡C— or a single bond, and particularly preferably —CH$_2$CH$_2$— or a single bond.

l preferably represents 1 or 2, and m preferably represents 0.

R² preferably represents a fluorine atom, cyano group, trifluoromethyl group, trifluoromethoxy group or linear alkyl or alkenyl group having 1 to 8 carbon atoms, more preferably a trifluoromethoxy group or fluorine atom, and particularly preferably a fluorine atom.

The specific structure of general formula (I) is preferably a compound represented by the following general formula (Ia)

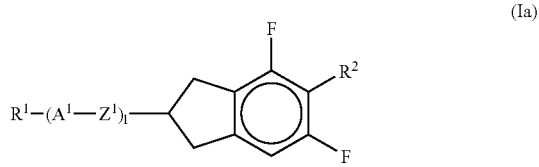

(Ia)

(wherein, R¹ represents an alkyl group having 1 to 15 carbon atoms, an alkenyl group having 2 to 15 carbon atoms, or a hydrogen atom, said alkyl group or alkenyl group may be non-substituted or have one or more fluorine atoms, chlorine atoms, methyl groups or trifluoromethyl groups as substituents, one or more methylene groups present in said alkyl group or alkenyl group may be substituted with —CO— or may be substituted with —S—, —O—, —OCOO—, —OCO— or —COO— in which the oxygen atoms are not mutually and directly bonded;

A¹ represents a group selected from the group consisting of:
(a1) a trans-1,4-cyclohexylene group (wherein one methylene group or two or more non-adjacent methylene groups present in this group may be substituted with —O— or —S—),
(b1) a 1,4-phenylene group (wherein one —CH= or two non-adjacent —CH= present in this group may be substituted with a nitrogen atom), and
(c1) a 1,4-cyclohexenylene group, 1,4-bicyclo(2.2.2)octylene group, piperidin-1,4-diyl group, naphthalen-2,6-diyl group, decahydronaphthalen-2,6-diyl group and 1,2,3,4-tetrahydronaphthalen-2,6-diyl group, and the groups of (a1), (b1) or (c1) may each be substituted with a cyano group, fluorine atom or chlorine atom;

l represents a number selected from the group of integers of 0 to 2;

Z¹ represents a group selected from the group consisting of —COO—, —OCO—, —CH₂O—, —OCH₂—, —CH₂CH₂—, —CH=CH—, —C≡C—, —(CH₂)₄—, —CH=CH—CH₂CH₂—, —CH₂CH₂—CH=CH— and a single bond;

R² represents a hydrogen atom, fluorine atom, chlorine atom, cyano group, trifluoromethyl group, fluoromethoxy group, difluoromethoxy group, trifluoromethoxy group, 2,2,2-trifluoroethyl group, alkyl group having 1 to 15 carbon atoms, alkenyl group having 2 to 15 carbon atoms or a hydrogen atom, said alkyl group or alkenyl group may be non-substituted or have one or more fluorine atoms, chlorine atoms, methyl groups or trifluoromethyl groups as substituents, and one or more methylene groups present in said alkyl group or alkenyl group may be substituted with —CO— or may be substituted with —S—, —O—, —OCOO—, —OCO— or —COO— in which the oxygen atoms are not mutually and directly bonded; and, in the case a plurality of A¹ and Z¹ are present, they may be the same or different), more preferably a compound represented by general formula (Ib), and particularly preferably a compound represented by the following formulas:

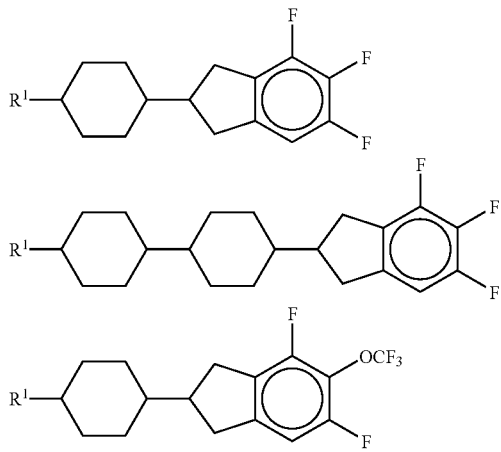

(wherein, R¹ represents an alkyl group or alkoxyl group having 1 to 8 carbon atoms).

A nematic liquid crystal composition of the present invention preferably contains represented by general formula (II) having a small absolute value of Δε:

(II)

(wherein, R³ and R⁴ respectively and independently represent an alkyl group having 1 to 15 carbon atoms, an alkenyl group having 2 to 15 carbon atoms, or a hydrogen atom, said alkyl group or alkenyl group may be non-substituted or have one or more fluorine atoms, chlorine atoms, methyl groups or trifluoromethyl groups as substituents, one or more methylene groups present in said alkyl group or alkenyl group may be substituted with —CO— or may be substituted with —S—, —O—, —OCOO—, —OCO— or —COO— in which the oxygen atoms are not mutually and directly bonded;

B¹, B² and B³ respectively and independently represent a group selected from the group consisting of:
(a1) a trans-1,4-cyclohexylene group (wherein one methylene group or two or more non-adjacent methylene groups present in this group may be substituted with —O— or —S—),
(b1) a 1,4-phenylene group (wherein one —CH= or two non-adjacent —CH= present in this group may be substituted with a nitrogen atom), and
(c1) a 1,4-cyclohexenylene group, 1,4-bicyclo(2.2.2)octylene group, piperidin-1,4-diyl group, naphthalen-2,6-diyl group, decahydronaphthalen-2,6-diyl group and 1,2,3,4-tetrahydronaphthalen-2,6-diyl group, and the groups of (a1), (b1) or (c1) may each be substituted with a cyano group, fluorine atom or chlorine atom;

o represents 0, 1 or 2;

L¹, L² and L³ respectively and independently represent a single bond, —CH₂CH₂—, —(CH₂)₄—, —OCH₂—, —CH₂O— or —C≡C—, and in the case a plurality of L² and B³ are present, they may be the same or different).

In general formula (II), R³ and R⁴ preferably represent a non-substituted linear alkyl group having 1 to 15 carbon atoms or a non-substituted linear alkenyl group having 2 to 15 carbon atoms, particularly preferably a non-substituted linear alkyl group having 1 to 8 carbon atoms or non-substituted linear alkenyl group having 2 to 6 carbon atoms, and even more preferably a structure represented by formulas (a) to (e) in the case of representing an alkenyl group. In addition, although $R^3$ and $R^4$ may be the same or different, $R^3$ and $R^4$ present in the same molecular are more preferably different.

$L^1$ and $L^2$ preferably represent —COO—, —OCO—, —CH$_2$CH$_2$—, —C≡C—, —(CH$_2$)$_4$— or a single bond, more preferably —CH$_2$CH$_2$—, —C≡C— or a single bond, and particularly preferably —CH$_2$CH$_2$— or a single bond. At least one of $L^1$ and $L^2$ preferably represents a single bond even when a plurality of $L^1$ and $L^2$ are present.

o preferably represents 0 or 1.

$B^1$, $B^2$ and $B^3$ respectively and independently preferably represent a trans-1,4-cyclohexylene group, 1,4-phenylene group, 3-fluoro-1,4-phenylene group or 3,5-difluoro-1,4-phenylene group, more preferably a trans-1,4-cyclohexylene group or 1,4-phenylene group, and preferably at least one of $B^1$, $B^2$ and $B^3$ represents a trans-1,4-cyclohexylene group.

A specific compound represented by general formula (II) is preferably a structure represented by the following general formula (IIa):

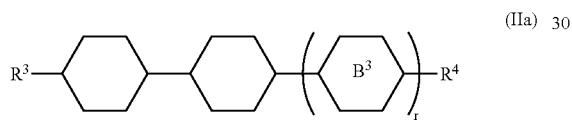

(IIa)

(wherein, $R^3$ and $R^4$ represent alkyl groups having 1 to 8 carbon atoms, alkoxyl groups having 1 to 8 carbon atoms, alkenyl groups having 2 to 8 carbon atoms or alkenyloxy groups having 3 to 16 carbon atoms, $B^3$ represents a 1,4-phenylene group or trans-1,4-cyclohexylene group, and r represents 0 or 1).

More specific compounds represented by general formula (II) are preferably structures represented by the following general formulas (II-1) to (II-3):

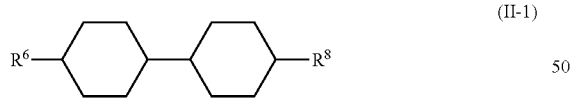

(II-1)

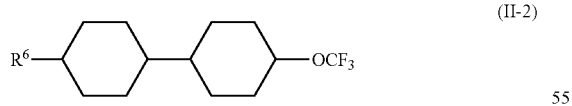

(II-2)

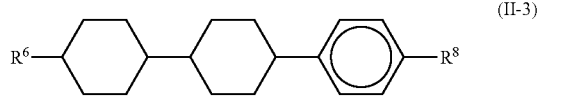

(II-3)

(wherein, $R^6$ and $R^8$ respectively and independently represent an alkyl group or alkoxyl group having 1 to 8 carbon atoms, alkenyl group having 2 to 8 carbon atoms, or alkenyloxy group having 3 to 16 carbon atoms).

In addition, structures represented by the following general formulas are also preferable.

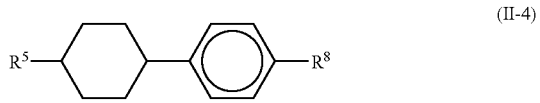

(II-4)

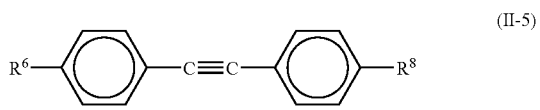

(II-5)

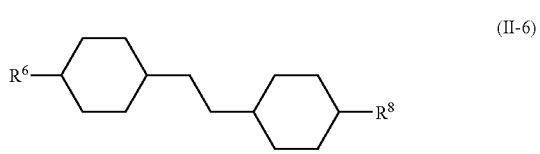

(II-6)

(II-7)

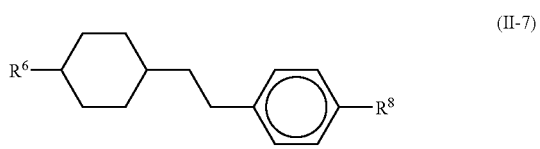

(II-8)

(II-9)

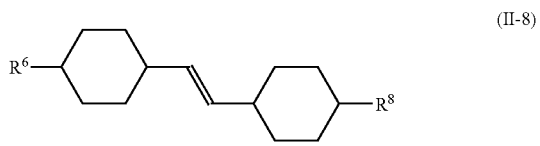

(II-10)

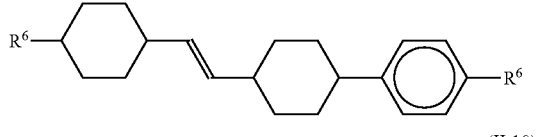

(II-11)

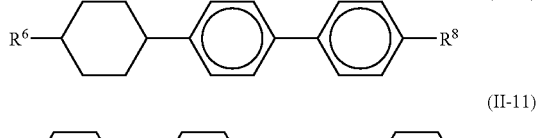

(wherein, $R^6$ and $R^8$ respectively and independently represent an alkyl group or alkoxyl group having 1 to 8 carbon atoms, alkenyl group having 2 to 8 carbon atoms, or alkenyloxy group having 3 to 16 carbon atoms).

Although a compound selected from general formula (II) has low viscosity and has the effect of improving response speed as a result of being contained, if its content is excessively large, there is the risk of increasing threshold voltage. In the case of containing a compound selected from general formula (II) in a liquid crystal composition, one type to six types are preferably contained, while one type to four types are particularly preferably contained.

The content of a compound represented with general formula (II) in a liquid crystal composition is preferably within the range of 10 to 80% by weight, and more preferably within the range of 10 to 60% by weight.

In the present invention, it is preferable contain compounds represented by the following general formulas (IIIa), (IIIb) and (IIIc), which have a comparatively large Δε:

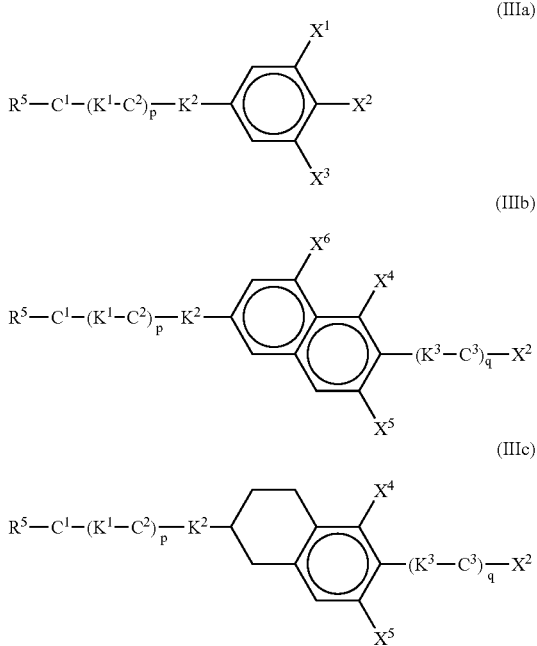

(wherein, R⁵ represents an alkyl group having 1 to 15 carbon atoms, an alkenyl group having 2 to 15 carbon atoms, or a hydrogen atom, said alkyl group or alkenyl group may be non-substituted or have one or more fluorine atoms, chlorine atoms, methyl groups or trifluoromethyl groups as substituents, one or more methylene groups present in said alkyl group or alkenyl group may be substituted with —CO— or may be substituted with —S—, —O—, —OCOO—, —OCO— or —COO— in which the oxygen atoms are not mutually and directly bonded;

$C^1$, $C^2$ and $C^3$ respectively and independently represent a group selected from the group consisting of:

(d1) a trans-1,4-cyclohexylene group (wherein one methylene group or two or more non-adjacent methylene groups present in this group may be substituted with —O— or —S—), (e1) a 1,4-phenylene group (wherein one —CH═ or two non-adjacent —CH═ present in this group may be substituted with a nitrogen atom), and (f1) a 1,4-cyclohexenylene group, 1,4-bicyclo(2.2.2)octylene group, piperidin-1,4-diyl group, naphthalen-2,6-diyl group, 1,2,3,4-tetrahydronaphthalen-2,6-diyl group and decahydronaphthalen-2,6-diyl group, and the groups of (d1), (e1) or (f1) may each be substituted with a cyano group, fluorine atom or chlorine atom;

$K^1$, $K^2$ and $K^3$ respectively and independently represent a single bond, —CH₂CH₂—, —(CH₂)₄—, —OCH₂—, —CH₂O—, —COO—, —OCO— or —C≡C—;

$X^1$, $X^3$, $X^4$, $X^5$ and $X^6$ respectively and independently represent a hydrogen atom or fluorine atom;

p and q respectively and independently represent 0, 1 or 2, and the sum of p and q is 2 or less; and, $X^2$ represents a hydrogen atom, fluorine atom, chlorine atom, cyano group, trifluoromethyl group, fluoromethoxy group, difluoromethoxy group, trifluoromethoxy group, 2,2,2-trifluoroethyl group, alkyl group having 1 to 15 carbon atoms, alkenyl group having 2 to 15 carbon atoms or a hydrogen atom, said alkyl group or alkenyl group may be non-substituted or have one or more fluorine atoms, chlorine atoms, methyl groups or trifluoromethyl groups as substituents, and one or more methylene groups present in said alkyl group or alkenyl group may be substituted with —CO— or may be substituted with —S—, —O—, —OCOO—, —OCO— or —COO— in which the oxygen atoms are not mutually and directly bonded).

In general formulas (IIIa), (IIIb) and (IIIc), $R^5$ preferably represents a linear alkyl group having 1 to 15 carbon atoms or an alkenyl group having 2 to 15 carbon atoms, more preferably represents a linear alkyl group having 1 to 10 carbon atoms or alkenyl group having 2 to 10 carbon atoms, particularly preferably a linear alkyl group having 1 to 8 carbon atoms or an alkenyl group having 2 to 6 carbon atoms, and even more preferably a structure represented by formulas (a) to (e) in the case of representing an alkenyl group. $K^1$, $K^2$ and $K^3$ preferably represent —COO—, —OCO—, —CH₂CH₂—, —C≡C—, —(CH₂)₄— or single bonds, more preferably —CH₂CH₂—, —C≡C— or single bonds, particularly preferably —CH₂CH₂— or single bonds, and even more preferably at least one of $K^1$, $K^2$ and $K^3$ represents a single bond when a plurality of $K^1$, $K^2$ and $K^3$ are present. p and q preferably represent 0 or 1. $C^1$, $C^2$ and $C^3$ respectively and independently preferably represent a trans-1,4-cyclohexylene group, 1,4-phenylene group, 3-fluoro-1,4-phenylene group or 3,5-difluoro-1,4-phenylene group, more preferably a trans-1,4-cyclohexylene group or 1,4-phenylene group, and particularly a trans-1,4-cyclohexylene group.

$X^2$ preferably represents a fluorine atom, cyano group, trifluoromethyl group, fluoromethoxy group, difluoromethoxy group or trifluoromethoxy group, and particularly preferably a fluorine atom.

More specifically, a structure represented by the following general formula (IIIa-1) is preferably represented:

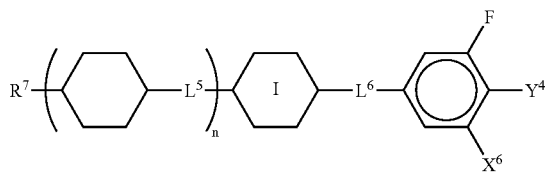

(wherein, R7 represents an alkyl group having 1 to 8 carbon atoms, an alkoxy group having 1 to 8 carbon atoms, or an alkenyl group having 2 to 8 carbon atoms, L5 and L6 respectively independently represent —CH₂CH₂—, —CH═CH—, —C≡C—, —(CH₂)₄— or a single bond, I represents a 1,4-phenylene group or trans-1,4-cyclohexylene group, X6 represents a hydrogen atom or fluorine atom, n represents 0 or 1, and Y4 represents a cyano group, fluorine atom, chlorine atom, trifluoromethyl group, fluoromethoxy group, difluoromethoxy group or trifluoromethoxy group).

More specifically, the structures represented by the following general formulas (IIIa-2a) to (IIIa-4d) are preferable:

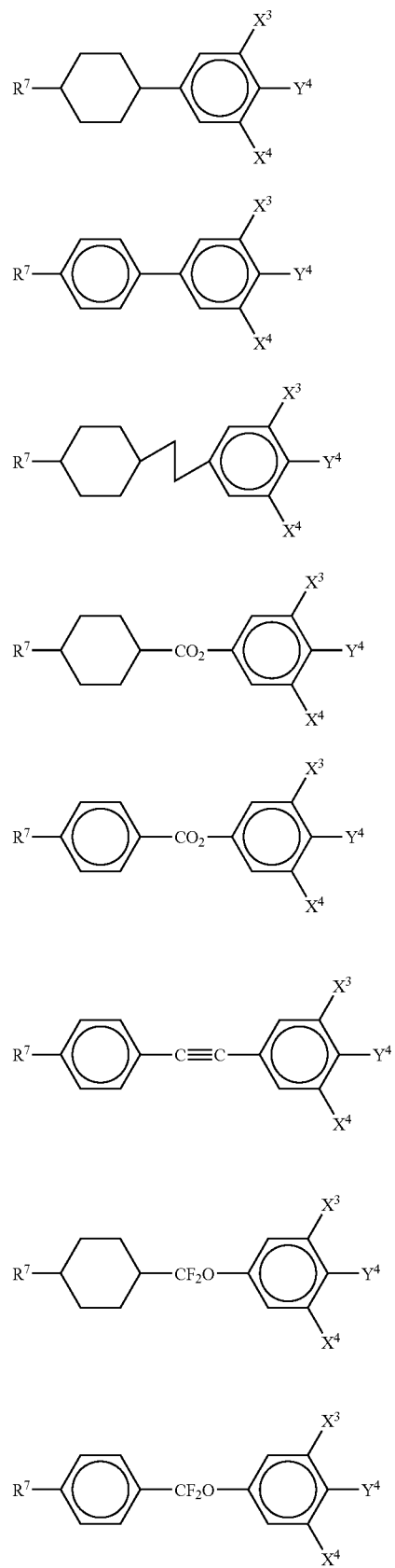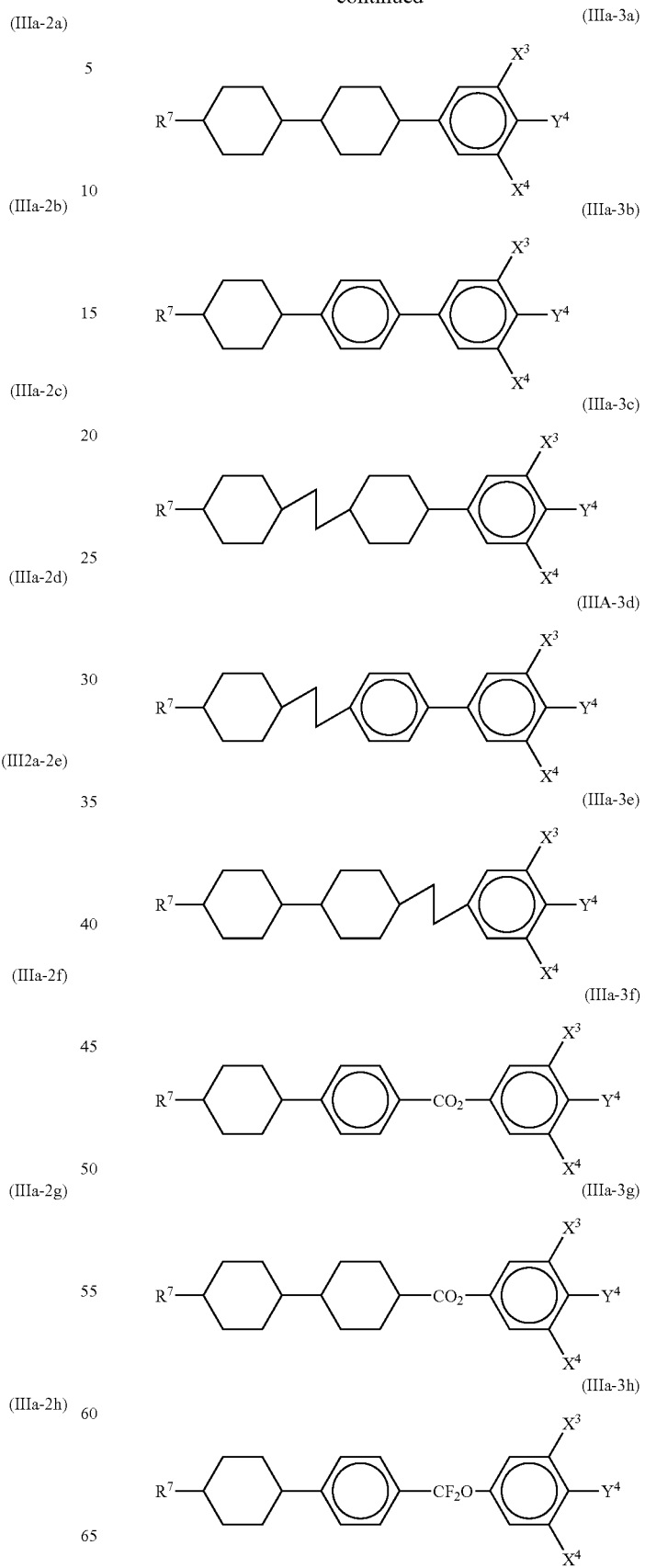

-continued

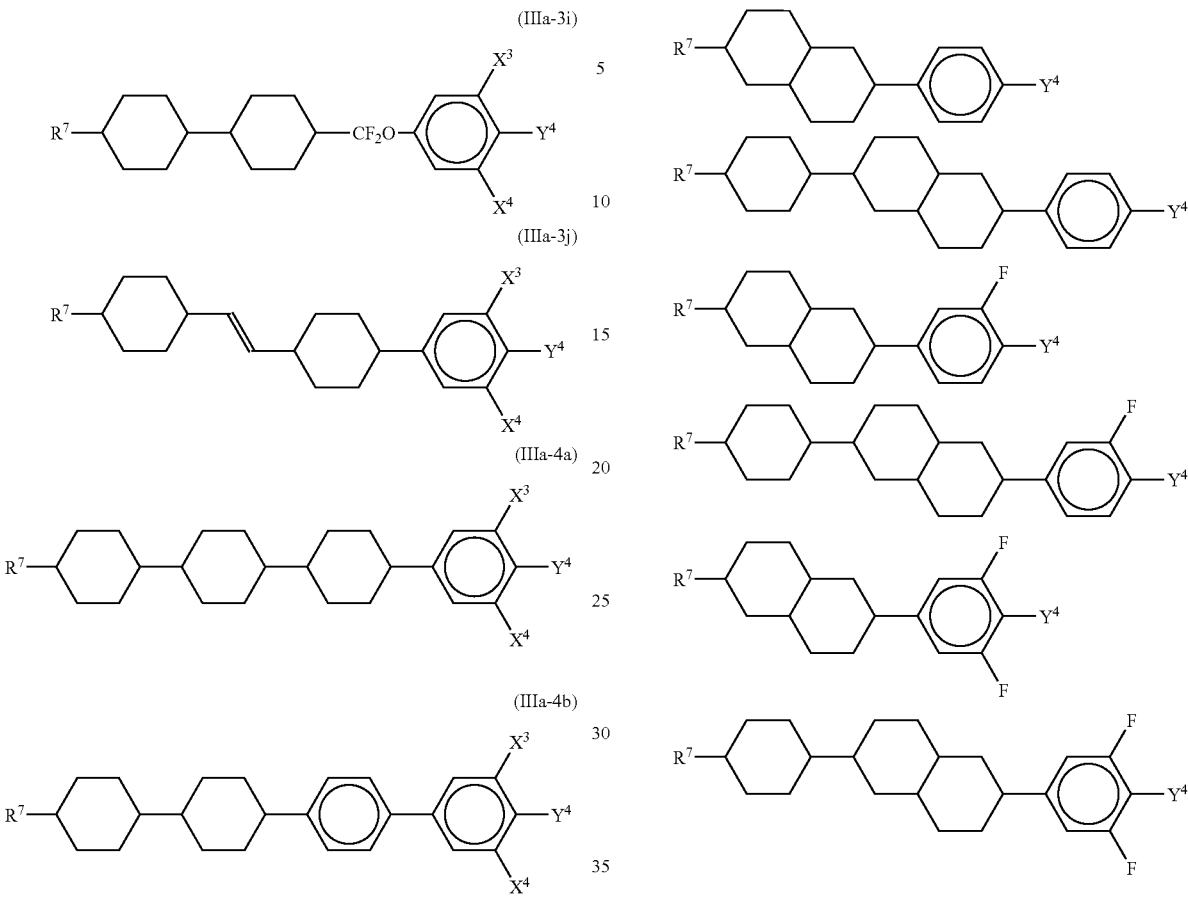

(wherein, $R^7$ represents an alkyl group having 1 to 8 carbon atoms, an alkoxy group having 1 to 8 carbon atoms, or an alkenyl group having 2 to 8 carbon atoms, $X^3$ and $X^4$ respectively and independently represent a hydrogen atom or a fluorine atom, and $Y^4$ represents a cyano group, fluorine atom, chlorine atom, trifluoromethyl group, fluoromethoxy group, difluoromethoxy group or trifluoromethoxy group); while the structures represented by the following general formulas are also preferable:

(wherein, $R^7$ represents an alkyl group having 1 to 8 carbon atoms, an alkoxy group having 1 to 8 carbon atoms, or an alkenyl group having 2 to 8 carbon atoms, $X^3$ and $X^4$ respectively and independently represent a hydrogen atom or a fluorine atom, and $Y^4$ represents a cyano group, fluorine atom, chlorine atom, trifluoromethyl group, fluoromethoxy group, difluoromethoxy group or trifluoromethoxy group).

The structures represented by the following general formulas are preferable as specific structures of general formula (IIIb):

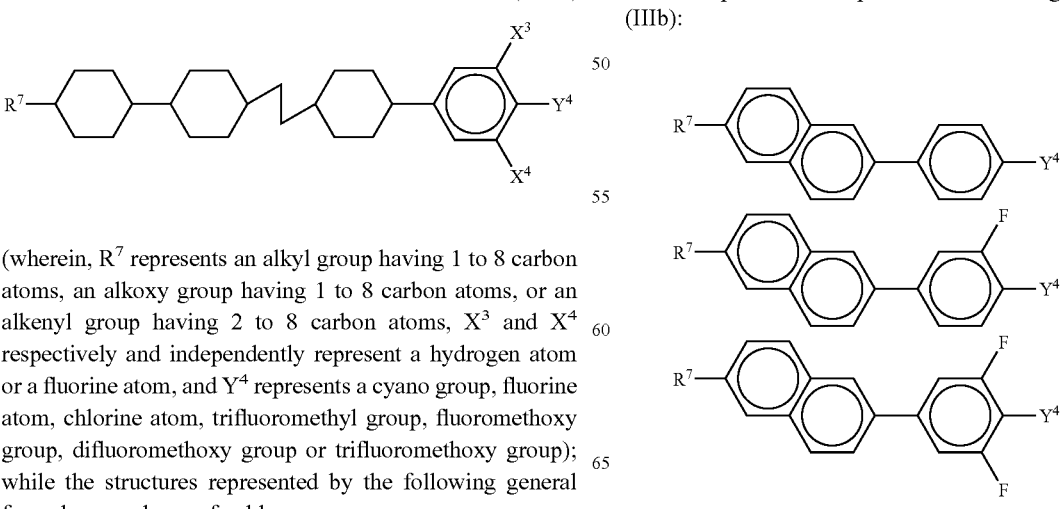

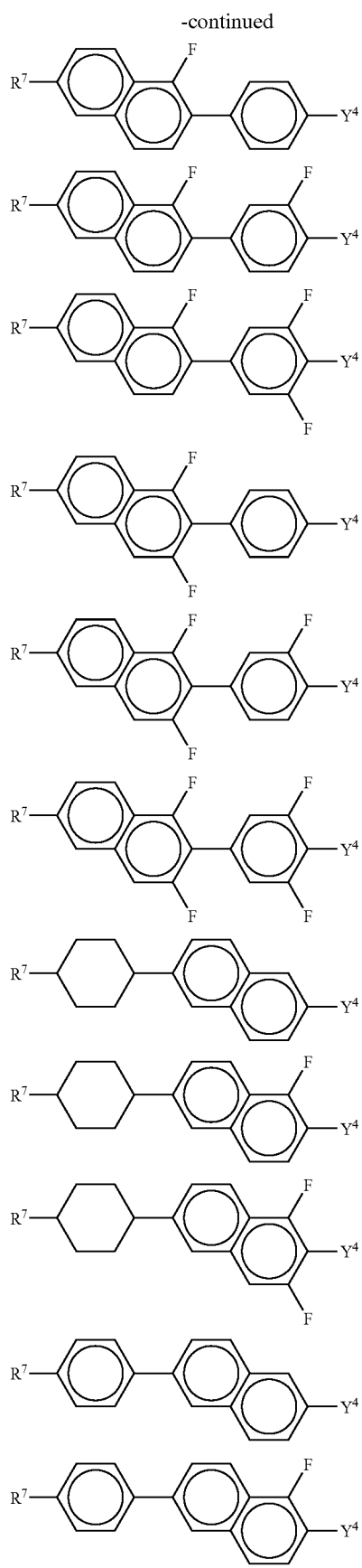
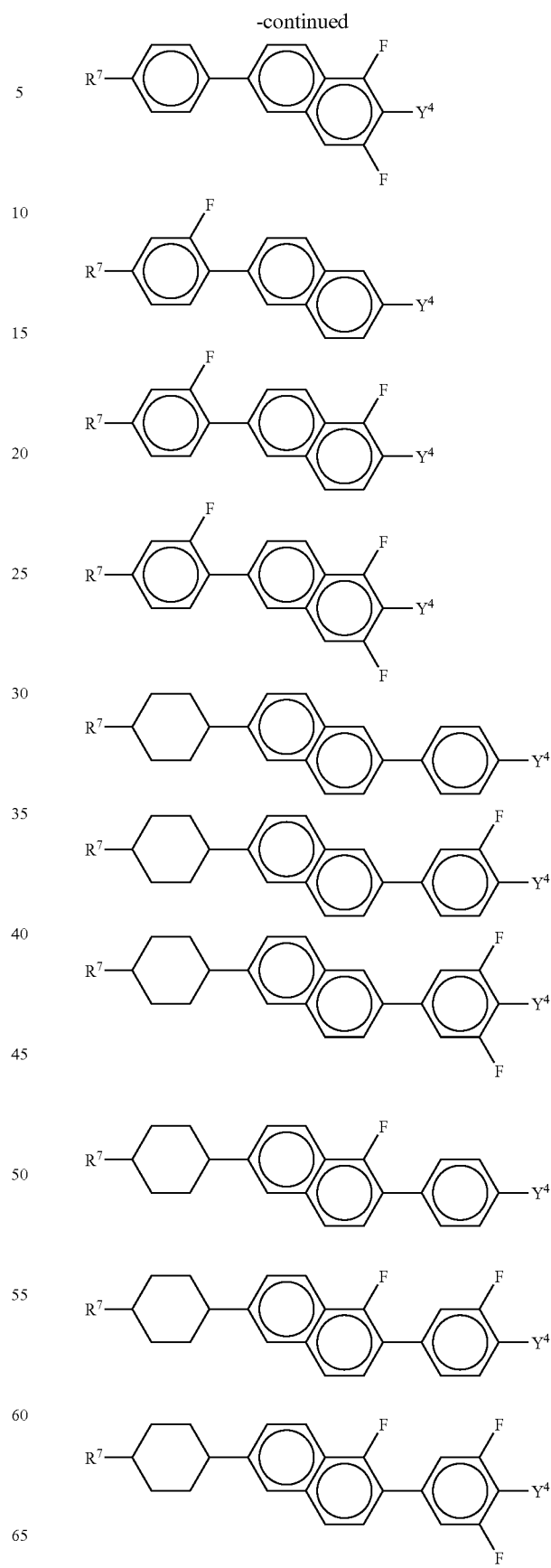

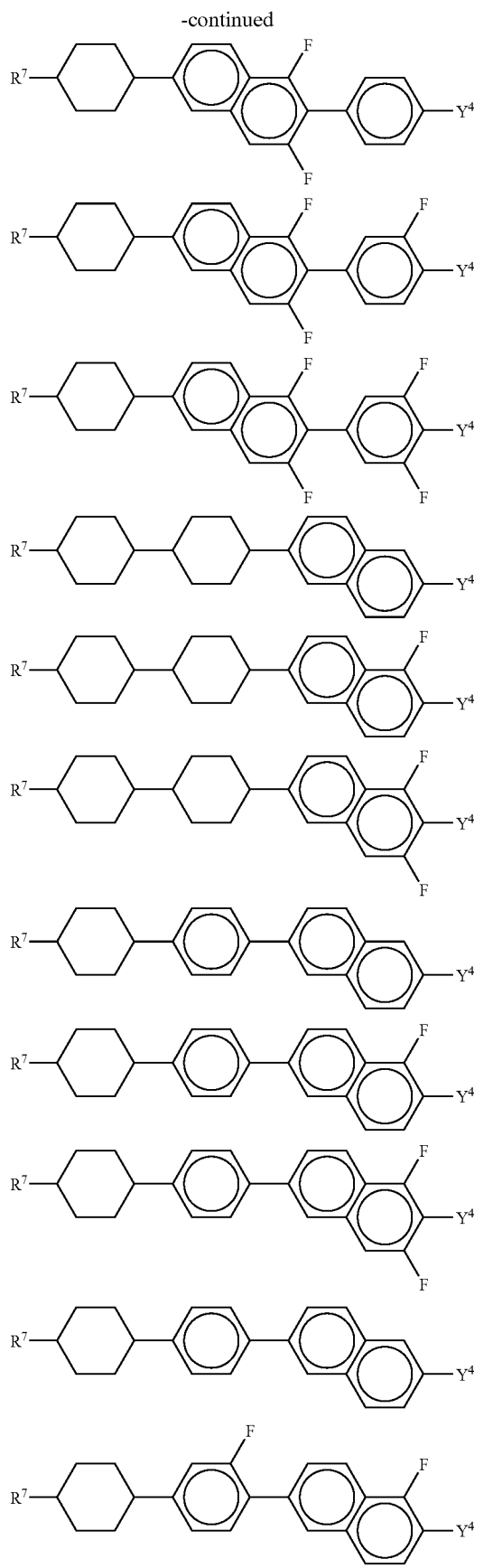

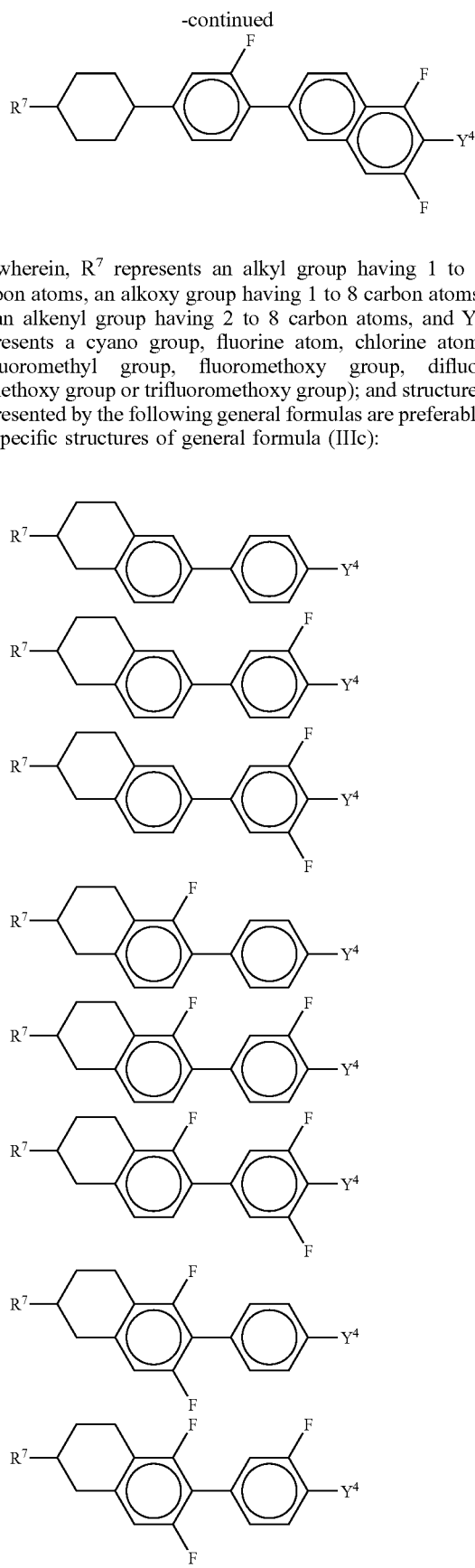

(wherein, $R^7$ represents an alkyl group having 1 to 8 carbon atoms, an alkoxy group having 1 to 8 carbon atoms, or an alkenyl group having 2 to 8 carbon atoms, and $Y^4$ represents a cyano group, fluorine atom, chlorine atom, trifluoromethyl group, fluoromethoxy group, difluoromethoxy group or trifluoromethoxy group); and structures represented by the following general formulas are preferable as specific structures of general formula (IIIc):

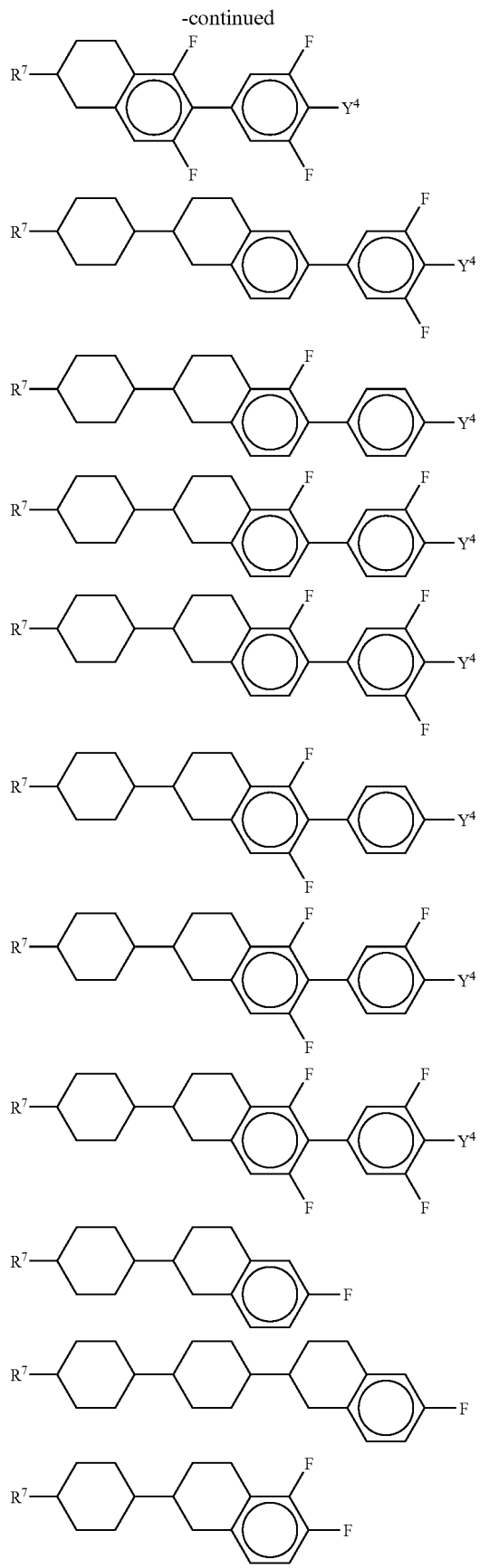

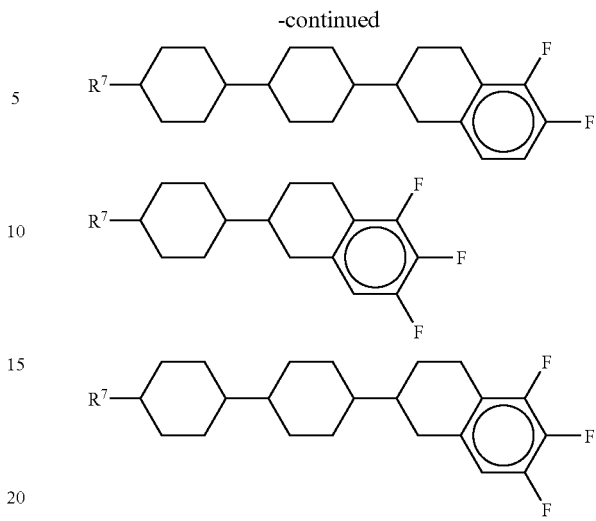

(wherein, $R^7$ represents an alkyl group having 1 to 8 carbon atoms, an alkoxy group having 1 to 8 carbon atoms, or an alkenyl group having 2 to 8 carbon atoms, and $Y^4$ represents a cyano group, fluorine atom, chlorine atom, trifluoromethyl group, fluoromethoxy group, difluoromethoxy group or trifluoromethoxy group).

Although a compound selected from the group consisting of compounds represented by general formulas (IIIa), (IIIb) and (IIIc) has a large $\Delta\epsilon$ and has the effect of lowering threshold voltage as a result of being contained in a nematic liquid crystal composition, if its content is excessively large, viscosity increases and response speed decreases. In the case of containing a compound selected from the group consisting of compounds represented by general formulas (IIIa), (IIIb) and (IIIc), preferably one to ten types are contained, and particularly preferably two to eight types are contained. In a nematic liquid crystal composition, the total content of the group consisting of compounds represented by general formulas (IIIa), (IIIb) and (IIIc) is preferably from 5 to 50% by weight, and more preferably 10 to 50% by weight.

A nematic liquid crystal composition of the present invention preferably contains at least one type of a compound represented by general formula (Ia), and contains at least one type of compound selected from the group consisting of compounds represented by general formulas (IIIa), (IIIb) and (IIIc), preferably contains at least one type of compound selected from the compounds represented by general formula (Ia), and contains at least one type of compound represented by general formula (II), more preferably contains at least one type of compound represented by general formula (Ia), at least one type of compound represented by general formula (II), and at least one type of compound selected from the group consisting of compounds represented by general formulas (IIIa), (IIIb) and (IIIc), and particularly preferably contains at least one type of compound selected from the compounds represented by general formula (Ia), at least one type of compound represented by general formula (II), and at least two types of compounds selected from the group consisting of compounds represented by general formulas (IIIa), (IIIb) and (IIIc).

In addition, a nematic liquid crystal composition of the present invention more preferably contains at least one type of compound selected from the compounds represented by general formula (Ia), at least one type of compound represented by general formula (II), at least one type of compound represented by general formula (IIIa), and at least one type of compound selected from the group consisting of compounds represented by general formulas (IIIb) and (IIIc), and the total content of the group consisting of compounds represented by general formulas (IIIa), (IIIb) and (IIIc) is within the range of 10 to 50% by weight.

A nematic liquid crystal composition of the present invention particularly preferably contains at least one type of a compound represented by general formula (Ib) and its total content is within the range of 5 to 50% by weight, contains at least one type of compound represented by general formula (IIb) and its total content is within the range of 10 to 60% by weight, and contains at least one type of compound selected from the group of compounds represented by general formulas (IIIa), (IIIb) and (IIIc) and its total content is within the range of 5 to 50% by weight.

In a nematic liquid crystal composition of the present invention, Δn is preferably within the range of 0.08 to 0.14, and more preferably within the range of 0.08 to 0.13.

Although a nematic liquid crystal composition of the present invention has a wide liquid crystal phase temperature range (absolute value of the difference between the liquid crystal phase lower limit temperature and liquid crystal phase upper limit temperature), the liquid crystal phase temperature range is preferably 95° C. or more, and more preferably 100° C. or more. In addition, the liquid crystal phase upper limit temperature is preferably 70° C. or higher, and more preferably 80° C. or higher. Moreover, the liquid crystal phase lower limit temperature is preferably −20° C. or lower, and more preferably −30° C. or lower.

Although the aforementioned nematic liquid crystal composition is useful for an active matrix liquid crystal display (AM-LCD) or super twist nematic liquid crystal display (STN-LCD), it is particularly useful for an AM-LCD, and can be used for backlit or reflective liquid crystal displays. A nematic liquid crystal composition of the present invention may also contain ordinary nematic liquid crystal, smectic liquid crystal, cholesteric liquid crystal and so forth in addition to the aforementioned compounds.

A compound represented by general formula (Ib) can be produced in the manner described below. After enolating an acetic ester derivative represented by general formula (IV):

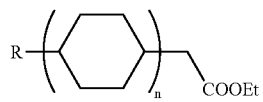

(IV)

(wherein, R represents an alkyl group having 1 to 12 carbon atoms or an alkenyl group having 2 to 12 carbon atoms, and n represents 1 or 2) using lithium diisopropylamide, lithium hexamethyl disilazide or butyl lithium and so forth, it is reacted with 3,4,5-trifluorobenzylbromide to obtain a compound represented by general formula (V):

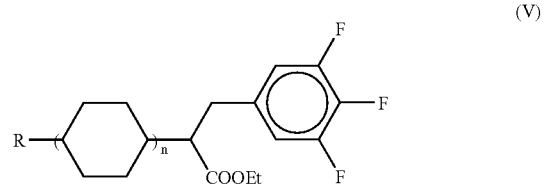

(V)

(wherein, R represents an alkyl group having 1 to 12 carbon atoms or an alkenyl group having 2 to 12 carbon atoms, and n represents 1 or 2). This compound is then hydrolyzed using a base such as sodium hydroxide or potassium hydroxide, and after converting the resulting carboxylic acid to an acid chloride using a chlorinating agent such as thionyl chloride, it is reacted with a Lewis acid such as aluminum chloride to obtain an indanone derivative represented by general formula (VI):

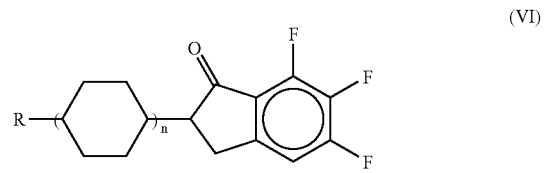

(VI)

(wherein, R represents an alkyl group having 1 to 12 carbon atoms or an alkenyl group having 2 to 12 carbon atoms, and n represents 1 or 2). This is then reduced using a reducing agent such as sodium borohydride or lithium aluminum hydride followed by heating the resulting alcohol derivative in the presence of an acid catalyst such as p-toluene sulfonic acid to obtain an indene derivative represented by general formula (VII):

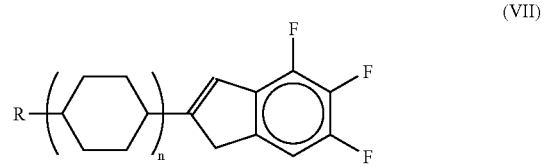

(VII)

(wherein, R represents an alkyl group having 1 to 12 carbon atoms or an alkenyl group having 2 to 12 carbon atoms, and n represents 1 or 2). This is then hydrogenated in the presence of a metal catalyst such as Pd—C, Rh—C, Pt—C or Pd(OH)$_2$ to obtain the target compound represented by general formula (Ib).

Although the following provides a more detailed description of the present invention through its examples, the present invention is not limited to these examples. In addition, the term "%" in the compositions of the following examples and comparative examples refers to "% by weight".

The characteristics measured in the examples are as indicated below.

Liquid crystal phase upper limit temperature ($T_{N-1}$): Nematic phase-isotropic liquid phase transition temperature (° C.)

Liquid crystal phase lower limit temperature ($T_{\to N}$): Solid phase or nematic phase-nematic phase transition temperature (° C.)

Nematic liquid crystal phase temperature range (ΔT): $|T_{N-1} - T_{\to N}|$

Vth: Threshold voltage when TN-LCD is composed with a cell thickness of 6 μm

Δ∈: Dielectric anisotropy

Δn: Refractive index anisotropy

η: Viscosity (mPa·s)

The following abbreviations are used to describe compounds.

Suffix n (number) $C_nH_{2n+1}$—
C Trans-1,4-cyclohexylene group
P 1,4-phenylene group
E —COO—
e —OCO—
A —CH$_2$CH$_2$—
t —C≡C—
CN —C≡N—
On —OC$_n$H$_{2n+1}$
F —F
OCFFF —OCF$_3$
ndm- $C_nH_{2n+1}$—C═C—(CH$_2$)$_{m-1}$—
—O(dm)n —O(CH$_2$)$_{m-2}$—C═C—$C_nH_{2n+1}$

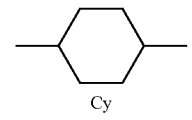
Cy

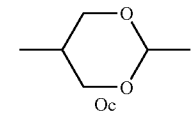
Oc

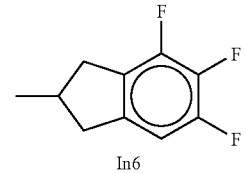
In6

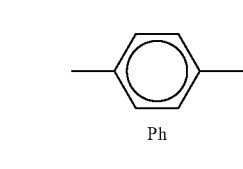
Ph

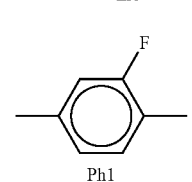
Ph1

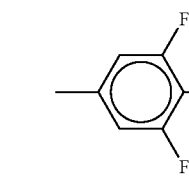
Ph3

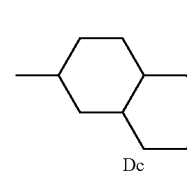
Dc

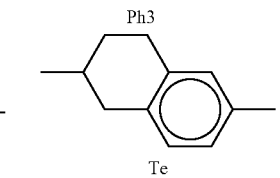
Te

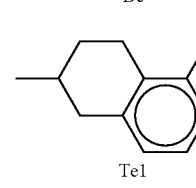
Te1

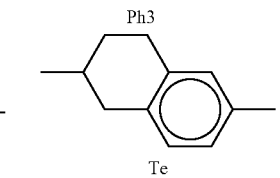
Ta1

-continued

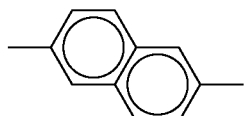
Np

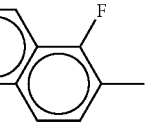
Np1

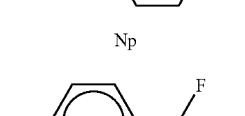
Na4

EXAMPLE 1

Synthesis of 4,5,6-trifluoro-2-(trans-4-propylcyclohexyl)indane (I-1)

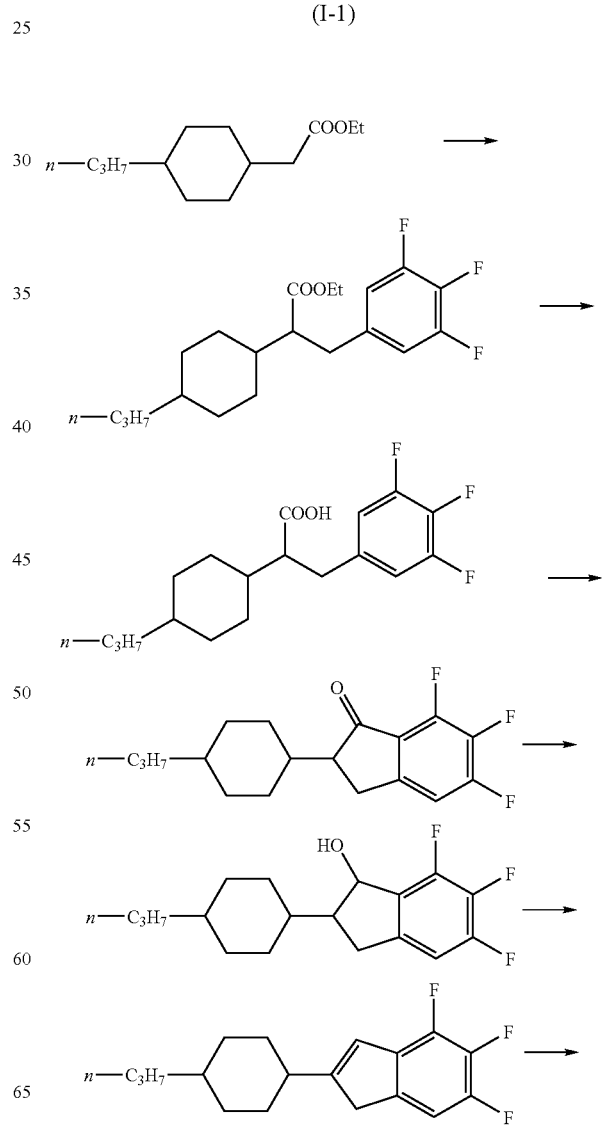

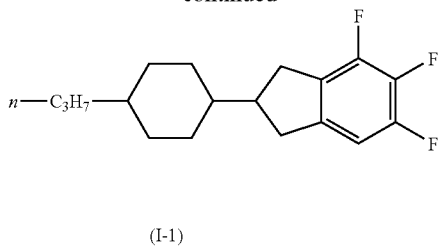

(I-1)

Dichloromethane (25 ml) and thionyl chloride (20 ml) were added to 2-(trans-4-propylcyclohexyl)-3-(3,4,5-trifluorophenyl)propionic acid crude product (12.3 g), and refluxed while heating for 4 hours. The dichloromethane was distilled off at normal pressure and the thionyl chloride was distilled off under reduced pressure followed by the addition of dichloromethane (50 ml) to the residue to prepare a dichloromethane solution of 2-(trans-4-propylcyclohexyl)-3-(3,4,5-trifluorophenyl)propionic acid chloride. This was then dropped in to a dichloromethane suspension (20 ml) of aluminum chloride (8 g) at room temperature over the course of 30 minutes. Moreover, after stirring for 2 hours, the reaction solution was poured into 10% hydrochloric acid while cooling with ice. The organic layer was concentrated after drying with anhydrous sodium sulfate. The residue was purified by silica gel column chromatography (hexane:ethyl acetate=20:1) to obtain 5,6,7-trifluoro-2-(trans-4-propylcyclohexyl)-1-indanone crude product (8.8 g, purity: 73%). This was then recrystallized from ethanol to obtain 5,6,7-trifluoro-2-(trans-4-propylcyclohexyl)-1-indanone (5 g, purity: 99%). This compound had a molecular weight of 310 as determined by mass analysis.

(1–4) Synthesis of 4,5,6-trifluoro-2-(trans-4-propylcyclohexyl)indene

Sodium borohydride (2 g) were added to an ethanol solution (50 ml) of 5,6,7-trifluoro-2-(trans-4-propylcyclohexyl)-1-indane (5 g) and stirred for 1 hour at room temperature. The reaction solution was poured into 10% hydrochloric acid and extracted with ethyl acetate followed by washing the organic layer with saturated saltwater, drying with anhydrous magnesium sulfate and concentrating. The reaction solution was returned to room temperature, washed with 10% hydrochloric acid and saturated saltwater, dried with anhydrous magnesium sulfate and concentrated. The residue was purified by silica gel column chromatography (hexane) to obtain 4,5,6-trifluoro-2-(trans-4-propylcyclohexyl)indene (4.5 g). This compound had a molecular weight of 294 as determined by mass analysis.

(1–5) Synthesis of 4,5,6-Trifluoro-2-(Trans-4-Propylcyclohexyl)Indane

Ethanol (70 ml), ethyl acetate (30 ml) and 5% palladium-carbon (450 mg) were added to 4,5,6-trifluoro-2-(trans-4-propylcyclohexyl)indene (4.5 g), and stirred for 1 hour in a hydrogen atmosphere. The reaction solution was filtered with celite, the filtrate was concentrated, and the residue was purified with a silica gel short column (hexane) to obtain 4,5,6-trifluoro-2-(trans-4-propylcyclohexyl)indane (4.5 g). Moreover, this was then recrystallized from ethanol to obtain 4,5,6-trifluoro-2-(trans-4-propylcyclohexyl)indane (4.5 g, purity: 99.8%). The melting point of this compound was 52° C.

$^1$H NMR: 3.0 (s,1H), 7.4–8.0 (m, 5H) MS m/z: 296 (M$^+$)

EXAMPLE 2

Synthesis of 4,5,6-trifluoro-2-(trans-4-(trans-4-propylcyclohexyl)cyclohexyl)indane 4,5,6-trifluoro-2-(trans-4-(trans-4-propylcyclohexyl)cyclohexyl)indane was obtained using the same procedure as Example 1 with the exception of using (trans-4-(trans-4-propylcyclohexyl)cyclohexyl)ethyl acetate for the starting material instead of the (trans-4-propylcyclohexyl)ethyl acetate in Example 1.

EXAMPLES 3, 4 AND COMPARATIVE EXAMPLES 1, 2

Preparation of Wide Temperature Range Liquid Crystal Compositions

Nematic liquid crystal compositions (Nos. 1 and 2) having the characteristic of a wide temperature range were prepared using the 4,5,6-trifluoro-2-(trans-4-propylcyclohexyl)indane (indicated as 3-Cy-In6 in the table) synthesized in Example 1. The compositions of the prepared liquid crystal compositions are shown in the following Table 1. These liquid crystal compositions were prepared to have a liquid crystal phase temperature range of about 140° C.

TABLE 1

| | | Examples 3 and 4 | | |
|---|---|---|---|---|
| | | Example 3 (No. 1) | | Example 4 (No. 2) |
| Composition | 2-Dc-Ph1-F | 15% | 2-Dc-Ph1-F | 5% |
| | 3-Ta1-Ph3-F | 7% | 3-Ta1-Ph3-F | 7% |
| | Od1-Cy-Cy-5 | 15% | Od1-Cy-Cy-5 | 15% |
| | 3-Cy-Cy-Ph-Ph1-F | 9% | 3-Cy-Cy-Ph-Ph1-F | 9% |
| | 4-Cy-Cy-Ph-Ph1-F | 9% | 4-Cy-Cy-Ph-Ph1-F | 9% |
| | 2-Cy-2-Cy-Cy-Ph1-F | 10% | 2-Cy-2-Cy-Cy-Ph1-F | 10% |
| | 3-Cy-2-Cy-Cy-Ph1-F | 10% | 3-Cy-2-Cy-Cy-Ph1-F | 10% |
| | 3-Cy-In6 | 25% | 3-Cy-In6 | 35% |

In order to compare physical properties, nematic liquid crystal compositions R-1 and R-2 of Comparative Examples 1 and 2 were prepared as shown in Table 2 as liquid crystal compositions having a wide temperature range.

TABLE 2

| | | Comparative Examples 1 and 2 | | |
|---|---|---|---|---|
| | | Comparative Example 1 (R1) | | Comparative Example 2 (R2) |
| Composition | 2-Dc-Ph1-F | 25% | 2-Dc-Ph1-F | — |
| | 3-Dc-Ph1-F | 15% | 3-Dc-Ph1-F | — |
| | 3-Ta1-Ph3-F | 7% | 3-Ta1-Ph3-F | 20% |
| | Od1-Cy-Cy-5 | 15% | Od1-Cy-Cy-5 | 20% |
| | Od3-Cy-Cy-3 | — | Od3-Cy-Cy-3 | — |
| | 3-Cy-Cy-Ph-Ph1-F | 9% | 3-Cy-Cy-Ph-Ph1-F | — |
| | 4-Cy-Cy-Ph-Ph1-F | 9% | 4-Cy-Cy-Ph-Ph1-F | 10% |
| | 2-Cy-2-Cy-Cy-Ph1-F | 10% | 2-Cy-2-Cy-Cy-Ph1-F | 10% |
| | 3-Cy-2-Cy-Cy-Ph1-F | 10% | 3-Cy-2-Cy-Cy-Ph1-F | 10% |
| | Od1-Cy-Cy-Ph-1 | — | Od1-Cy-Cy-Ph-1 | 10% |
| | Od3-Cy-Cy-Ph-1 | — | Od3-Cy-Cy-Ph-1 | 10% |

The physical property values of Examples 3 and 4 and Comparative Examples 1 and 2 are shown in Table 3.

TABLE 3

Physical Properties of Examples 3 and 4 and Comparative Examples 1 and 2

|  | Example 3 | Example 4 | Comp. Ex. 1 | Comp. Ex. 2 |
|---|---|---|---|---|
| ΔT | 145 | 145 | 138 | 95 |
| $T_{N-1}$ (° C.) | 95 | 100 | 88 | 95 |
| $T_{\to N}$ (° C.) | −50 | −45 | −50 | 0 |
| Δε | 6.6 | 7.0 | 5.5 | 4.9 |
| Δn | 0.086 | 0.089 | 0.080 | 0.078 |

As shown in Table 3, the nematic liquid crystal compositions of Examples 3 and 4 can be understood to have a low liquid crystal phase lower limit temperature ($T_{\to N}$), high liquid crystal phase upper limit temperature ($T_{N-1}$) and wide liquid crystal temperature range.

These nematic liquid crystal compositions can be used to produce TFT liquid crystal display elements having superior display quality.

Although the nematic liquid crystal composition of Comparative Example 1 has a composition comparatively close to that of the present invention and the liquid crystal phase temperature range is also quite close, the liquid crystal phase upper limit temperature is inferior to that of Examples 3 and 4. In addition, since the dielectric anisotropy of the nematic liquid crystal composition of Comparative Example 1 is lower than that of Examples 3 and 4 of the present invention, the threshold voltage characteristics of a TFT liquid crystal display element produced using the nematic liquid crystal composition of Comparative Example 1 are inferior to that produced using Examples 3 and 4 of the present invention.

Although the liquid crystal composition of Comparative Example 2, in which the liquid crystal phase upper limit temperature has been made to approach that of a liquid crystal composition of the present invention, has a liquid crystal phase upper limit temperature that is equal to that of Example 1, since the liquid crystal phase lower limit temperature is considerably higher, it is considerably inferior in terms of the temperature range.

EXAMPLES 5, 6 AND COMPARATIVE EXAMPLES 3, 4

Preparation of Low Viscosity Liquid Crystal Compositions

Nematic liquid crystal compositions (Nos. 3 and 4) were prepared as shown in Table 4 as low viscosity liquid crystal compositions.

These liquid crystal compositions were prepared to have a target value of Δε of 5 to 6 and a viscosity of 16 mPa·s.

TABLE 4

Compositions of Examples 5 and 6

| | Example 5 (No. 3) | | Example 6 (No. 4) | |
|---|---|---|---|---|
| Compo- | 5-Cy-Cy-OCFFF | 9% | 5-Cy-Cy-OCFFF | 9% |
| sition | Od3-Ph-t-Ph-Od3 | 3% | Od3-Ph-t-Ph-Od3 | 8% |
| | Od1-Cy-Cy-5 | 20% | Od1-Cy-Cy-5 | 9% |
| | Od3-Cy-Cy-3 | 10% | Od3-Cy-Cy-3 | — |
| | Od1-Cy-Cy-Ph-1 | 7% | Od1-Cy-Cy-Ph-1 | 15% |
| | Od1-Cy-Cy-Ph1-f | — | Od1-Cy-Cy-Ph1-f | 24% |
| | 3-Cy-Ph-Na4-F | 16% | 3-Cy-Ph-Na4-F | — |
| | 3-Cy-Cy-Ph-Ph1-F | 4% | 3-Cy-Cy-Ph-Ph1-F | 4% |
| | 4-Cy-Cy-Ph-Ph1-F | 4% | 4-Cy-Cy-Ph-Ph1-F | 4% |

TABLE 4-continued

Compositions of Examples 5 and 6

| | Example 5 (No. 3) | | Example 6 (No. 4) | |
|---|---|---|---|---|
| | 2-Cy-In6 | 12% | 2-Cy-In6 | 12% |
| | 3-Cy-In6 | 15% | 3-Cy-In6 | 15% |

In order to compare physical properties, nematic liquid crystal compositions R-3 and R-4 of Comparative Examples 3 and 4 were prepared as shown in Table 5 as low viscosity liquid crystal compositions.

TABLE 5

Comparative Examples 3 and 4

| | Comparative Example 3 (R3) | | Comparative Example 4 (R4) | |
|---|---|---|---|---|
| Compo- | 2-Dc-Ph1-F | 13% | 3-Np1-Ph3-F | 11% |
| sition | 3-Ta1-Ph3-F | 6% | 5-Cy-E-Ph1-F | 6% |
| | 2-Cy-Np1-Ph3-F | 9% | Od1-Cy-Cy-5 | 20% |
| | 3-Cy-Np1-Ph3-F | 9% | Od3-Cy-Cy-3 | 20% |
| | Od1-Cy-Cy-5 | 20% | 3-Cy-Ph-O2 | 3% |
| | Od3-Cy-Cy-3 | 20% | 103-Oc-Cy-Ph1-F | 10% |
| | 3-Cy-Ph-O2 | 5% | 3-Cy-2-Cy-E-Ph1-F | 9% |
| | 2-Cy-Cy-Ph-Ph1-F | 6% | 4-Cy-2-Cy-E-Ph1-F | 9% |
| | 3-Cy-Cy-Ph-Ph1-F | 6% | 3-Cy-Cy-E-Ph1-F | 10% |
| | 4-Cy-Cy-Ph-Ph1-F | 6% | Od1-Cy-Cy-Ph-1 | 2% |

The physical property values of Examples 5 and 6 and Comparative Examples 3 and 4 are shown in Table 6. Table 6 Physical Properties of Examples 5 and 6 and Comparative Examples 3 and 4

|  | Example 5 | Example 6 | Comp. Ex. 3 | Comp. Ex. 4 |
|---|---|---|---|---|
| ΔT | 129 | 128 | 110 | 86 |
| $T_{N-1}$ (° C.) | 81 | 79 | 85 | 72 |
| $T_{\to N}$ (° C.) | −48 | −49 | −25 | −14 |
| Δε | 5.4 | 5.0 | 5.5 | 5.6 |
| Δn | 0.098 | 0.098 | 0.097 | 0.075 |
| η (mPa·s) | 15.6 | 15.8 | 22.0 | 16.4 |

As shown in Table 6, the nematic liquid crystal compositions of Examples 5 and 6 can be understood to have sufficiently large dielectric anisotropy for use as low viscosity liquid crystal compositions, and have a low liquid crystal phase lower limit temperature ($T_{\to N}$), high liquid crystal phase upper limit temperature ($T_{N-1}$) and wide liquid crystal temperature range.

These nematic liquid crystal compositions can be used to produce TFT liquid crystal display elements having superior display quality and high-speed response.

Although the nematic liquid crystal composition of Comparative Example 3 has a composition comparatively close to Examples 5 and 6, viscosity is not lowered to the value required for a liquid crystal composition of a low-viscosity system, while also having an inferior liquid crystal phase temperature range.

As shown for Comparative Example 4, in the case of viscosity being made to approach the liquid crystal compositions of Examples 5 and 6, the liquid crystal phase temperature range can be understood to become extremely narrow.

EXAMPLE 7 AND COMPARATIVE EXAMPLE 5

Preparation of Liquid Crystal Compositions

A nematic liquid crystal composition shown below (No. 5) was prepared and its physical property values were measured. Those results are shown in Table 7. In addition, a nematic liquid crystal composition of Comparative Example 5 was prepared, and its physical property values are also shown in Table 7.

These liquid crystal compositions were prepared to have a value of Δn in the vicinity of 0.12.

TABLE 7

Example 7 and Comparative Example 5

| | Example 7 (No. 5) | | Comparative Example 5 (R5) | |
|---|---|---|---|---|
| 2-Dc-Ph1-F | | 2% | 2-Dc-Ph1-F | 7% |
| 3-Np1-Ph-F | | — | 3-Np1-Ph-F | 2% |
| 3-Np1-Ph-1F | | — | 3-Np1-Ph-1F | 15% |
| Od3-Ph-t-Ph-Od3 | | 13% | Od3-Ph-t-Ph-Od3 | 4% |
| Od1-Cy-Cy-5 | | 24% | Od1-Cy-Cy-5 | 24% |
| Od3-Cy-Cy-3 | | 9% | Od3-Cy-Cy-3 | 18% |
| 3-Cy-Ph1-Na4-F | | 16% | 3-Cy-Ph1-Na4--F | 16% |
| 3-Cy-Cy-Ph-Ph1-F | | 6% | 3-Cy-Cy-Ph-Ph1-F | 7% |
| 4-Cy-Cy-Ph-Ph1-F | | 6% | 4-Cy-Cy-Ph-Ph1-F | 7% |
| 3-Cy-In6 | | 24% | 3-Cy-In6 | — |
| ΔT | 132 | | 112 | |
| $T_{N-1}$(° C.) | 82 | | 86 | |
| $T_{\to N}$(° C.) | −50 | | −26 | |
| Δε | 5.5 | | 5.5 | |
| Δn | 0.119 | | 0.119 | |
| η(mPa · s) | 15.6 | | 18.2 | |

Although the liquid crystal composition of Example 7 has a comparatively large value for Δn, it has both a sufficiently wide liquid crystal phase temperature range as well as low viscosity.

Although the liquid crystal composition of Comparative Example 5 has a similar value for Δn, it is somewhat inferior to the liquid crystal composition of Example 7 in terms of the liquid crystal phase temperature range and viscosity.

While preferred embodiments of the present invention have been described and illustrated above, it should be understood that these are exemplary of the present invention and are not to be considered as limiting. Additions, omissions, substitutions and other modifications can be made without departing from the spirit or scope of the present invention. Accordingly, the invention is not to be considered as being limited by the foregoing description, and is only limited by the scope of the appended claims.

INDUSTRIAL APPLICABILITY

The use of a nematic liquid crystal composition of the present invention makes it possible to provide a nematic liquid crystal composition having satisfactory liquid crystal characteristics such as response speed and threshold voltage, low liquid crystal phase lower limit temperature, high liquid crystal phase upper limit temperature and a wide liquid crystal phase temperature range by using a 4,6-difluoroindane-based compound.

The invention claimed is:

1. A nematic liquid crystal composition containing one or more types of a compound having a 4,6-difluoroindan-2,5-diyl group; wherein, the 5-position of this compound may be substituted with a hydrogen atom, fluorine atom, chlorine atom, cyano group, trifluoromethyl group, fluoromethoxy group, difluoromethoxy group, trifluoromethoxy group, 2,2,2-trifluoroethyl group, alkyl group having 1 to 15 carbon atoms, alkenyl group having 2 to 15 carbon atoms or a hydrogen atom, said alkyl group or alkenyl group may be non-substituted or have one or more fluorine atoms, chlorine atoms, methyl groups or trifluoromethyl groups as substituents, and one or more methylene groups present in said alkyl group or alkenyl group may be substituted with —CO— or may be substituted with —S—, —O—, —OCOO—, —OCO— or —COO— in which the oxygen atoms are not mutually and directly bonded;

the refractive index anisotropy is within the range of 0.08 to 0.15;

the liquid crystal phase upper limit temperature is 70° C. or higher;

the liquid crystal phase lower limit temperature is −20° C. or lower; and the difference between the liquid crystal phase upper limit temperature and liquid crystal phase lower limit temperature is 90° C. or more.

2. The nematic liquid crystal composition according to claim 1 wherein the compound having a 4,6-difluoroindan-2,5-diyl group is a compound represented by general formula (Ia):

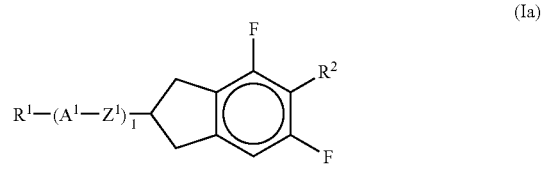

(Ia)

(wherein, $R^1$ represents an alkyl group having 1 to 15 carbon atoms, an alkenyl group having 2 to 15 carbon atoms, or a hydrogen atom, and said alkyl group or alkenyl group may be non-substituted or have one or more fluorine atoms, chlorine atoms, methyl groups or trifluoromethyl groups as substituents, and one or more methylene groups present in said alkyl group or alkenyl group may be substituted with —CO— or may be substituted with —S—, —O—, —OCOO—, —OCO— or —COO— in which the oxygen atoms are not mutually and directly bonded;

$A^1$ represents a group selected from the group consisting of:

(a1) a trans-1,4-cyclohexylene group (wherein one methylene group or two or more non-adjacent methylene groups present in this group may be substituted with —O— or —S—), (b1) a 1,4-phenylene group (wherein one —CH═ or two non-adjacent —CH═ present in this group may be substituted with a nitrogen atom), and (c1) a 1,4-cyclohexenylene group, 1,4-bicyclo(2.2.2)octylene group, piperidin-1,4-diyl group, naphthalen-2,6-diyl group, decahydronaphthalen-2,6-diyl group and 1,2,3,4-tetrahydronaphthalen-2,6-diyl group, and the groups of (a1), (b1) or (c1) may each be substituted with a cyano group, fluorine atom or chlorine atom;

l represents 0, 1 or 2;

$Z^1$ represents a group selected from the group selected from the group consisting of —COO—, —OCO—, —CH₂O—, —OCH₂—, —CH₂CH₂—, —CH═CH—, —C≡C—, —(CH$_2$)$_4$—, —CH=CH—CH$_2$CH$_2$—, —CH$_2$CH$_2$—CH=CH— and a single bond; and, R$^2$ represents a hydrogen atom, fluorine atom, chlorine atom, cyano group, trifluoromethyl group, fluoromethoxy group, difluoromethoxy group, trifluoromethoxy group, 2,2,2-trifluoroethyl group, alkyl group having 1 to 15 carbon atoms, alkenyl group having 2 to 15 carbon atoms or a hydrogen atom, and said alkyl group or alkenyl group may be non-substituted or have one or more fluorine atoms, chlorine atoms, methyl groups or trifluoromethyl groups as substituents, and one or more methylene groups present in said alkyl group or alkenyl group may be substituted with —CO— or may be substituted with —S—, —O—, —OCOO—, —OCO— or —COO— in which the oxygen atoms are not mutually and directly bonded; and in the case a plurality of A$^1$ and Z$^1$ are present, they may be the same or different).

3. The nematic liquid crystal composition according to claim 2 wherein the content of the compound represented by the general formula (Ia) is within the range of 5 to 50% by weight.

4. The nematic liquid crystal composition according to claim 1 or 2, further containing at least one type of compound represented by general formula (II):

R$^3$—B$^1$-L$^1$-B$^2$-(L$^2$-B$^3$)$_o$-R$^4$ (II)

(wherein, R$^3$ and R$^4$ respectively and independently represent an alkyl group having 1 to 15 carbon atoms, an alkenyl group having 2 to 15 carbon atoms, or a hydrogen atom, and said alkyl group or alkenyl group may be non-substituted or have one or more fluorine atoms, chlorine atoms, methyl groups or trifluoromethyl groups as substituents, and one or more methylene groups present in said alkyl group or alkenyl group may be substituted with —CO— or may be substituted with —S—, —O—, —OCOO—, —OCO— or —COO— in which the oxygen atoms are not mutually and directly bonded;

B$^1$, B$^2$ and B$^3$ respectively and independently represent a group selected from the group consisting of:

(a1) a trans-1,4-cyclohexylene group (wherein one methylene group or two or more non-adjacent methylene groups present in this group may be substituted with —O— or —S—), (b1) a 1,4-phenylene group (wherein one —CH= or two non-adjacent —CH= present in this group may be substituted with a nitrogen atom), and (c1) a 1,4-cyclohexenylene group, 1,4-bicyclo(2.2.2) octylene group, piperidin-1,4-diyl group, naphthalen-2,6-diyl group, decahydronaphthalen-2,6-diyl group and 1,2,3,4-tetrahydro-naphthalen-2,6-diyl group, and the groups of (a1), (b1) or (c1) may each be substituted with a cyano group, fluorine atom or chlorine atom;

o represents 0, 1 or 2;

L$^1$ and L$^2$ respectively and independently represent a single bond, —CH$_2$CH$_2$—, —(CH$_2$)$_4$—, —OCH$_2$—, —CH$_2$O— or —C≡C—; and in the case a plurality of L$^2$ and B$^3$ are present, they may be the same or different).

5. The nematic liquid crystal composition according to claim 1 or 2, further containing at least one type of a compound selected from the group consisting of compounds represented by generals formula (IIIa), (IIIb) and (IIIc):

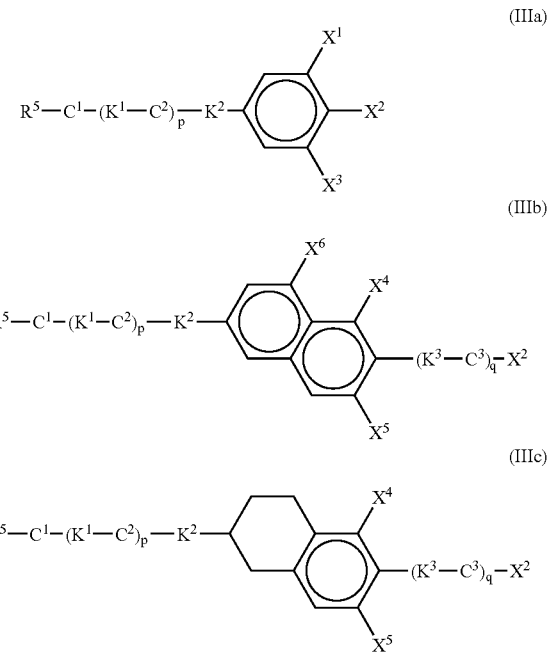

(wherein, R$^5$ represents an alkyl group having 1 to 15 carbon atoms, an alkenyl group having 2 to 15 carbon atoms, or a hydrogen atom in general formula (I), and said alkyl group or alkenyl group may be non-substituted or have one or more fluorine atoms, chlorine atoms, methyl groups or trifluoromethyl groups as substituents, and one or more methylene groups present in said alkyl group or alkenyl group may be substituted with —CO— or may be substituted with —S—, —O—, —OCOO—, —OCO— or —COO— in which the oxygen atoms are not mutually and directly bonded;

C$^1$, C$^2$ and C$^3$ respectively and independently represent a group selected from the group consisting of:

(d1) a trans-1,4-cyclohexylene group (wherein one methylene group or two or more non-adjacent methylene groups present in this group may be substituted with —O— or —S—), (e1) a 1,4-phenylene group (wherein one —CH= or two non-adjacent —CH= present in this group may be substituted with a nitrogen atom), and (f1) a 1,4-cyclohexenylene group, 1,4-bicyclo(2.2.2) octylene group, piperidin-1,4-diyl group, naphthalen-2,6-diyl group, 1,2,3,4-tetrahydronaphthalen-2, 6-diyl group and decahydronaphthalen-2,6-diyl group, and the groups of (d1), (e1) or (f1) may each be substituted with a cyano group, fluorine atom or chlorine atom;

K$^1$, K$^2$ and K$^3$ respectively and independently represent a single bond, —CH$_2$CH$_2$—, —(CH$_2$)$_4$—, —OCH$_2$—, —CH$_2$O—, —COO—OCO— or —C≡C—;

X$^1$, X$^3$, X$^4$, X$^5$ and X$^6$ respectively and independently represent a hydrogen atom or fluorine atom;

p and q respectively and independently represent 0, 1 or 2, and the sum of p and q is 2 or less; and, X$^2$ represents a hydrogen atom, fluorine atom, chlorine atom, cyano group, trifluoromethyl group, fluoromethoxy group, difluoromethoxy group, trifluoromethoxy group, 2,2,2-trifluoroethyl group, alkyl group having 1 to 15 carbon atoms, alkenyl group having 2 to 15 carbon atoms or a hydrogen atom, and said alkyl group or alkenyl group may be non-substituted or have one or more fluorine atoms, chlorine atoms, methyl groups or trifluoromethyl groups as substituents, and one or more methylene groups present in said alkyl group or alkenyl group may be substituted with —CO— or may be substituted with —S—, —O—, —OCOO—, —OCO— or —COO— in which the oxygen atoms are not mutually and directly bonded).

6. The nematic liquid crystal composition according to claim 5 wherein the total content of the compounds selected from the group consisting of the general formulas (IIIa), (IIIb) and (IIIc) is within the range of 10 to 50% by weight.

7. The nematic liquid crystal composition according to claim 4 further containing a compound represented by general formula (IIa):

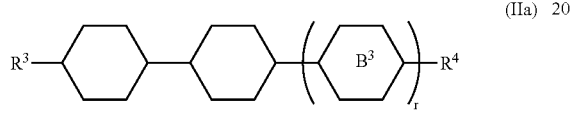

(IIa)

(wherein, $R^3$ and $R^4$ represent alkyl groups having 1 to 8 carbon atoms, alkoxyl groups having 1 to 8 carbon atoms, alkenyl groups having 2 to 8 carbon atoms or alkenyloxy groups having 3 to 16 carbon atoms, $B^3$ represents a 1,4-phenylene group or trans-1,4-cyclohexylene group, and r represents 0 or 1).

8. The nematic liquid crystal composition according to claim 7 wherein the content of the compound represented by the general formula (IIa) is within the range of 10 to 80% by weight.

9. The nematic liquid crystal compound according to claim 5 wherein the compound having a 4,6-difluoroindan-2,5-diyl group is a compound represented by general formula (Ib):

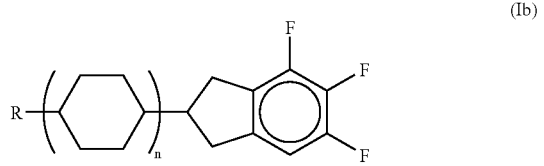

(Ib)

(wherein, R represents an alkyl group having 1 to 12 carbon atoms or an alkenyl group having 2 to 12 carbon atoms, and n represents 1 or 2).

10. The nematic liquid crystal composition according to claim 9, further containing at least one type of a compound represented by general formula (ha):

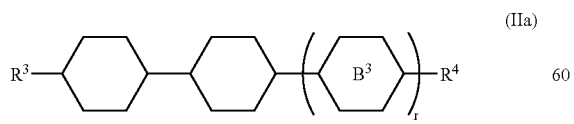

(IIa)

(wherein, $R^3$ and $R^4$ represent alkyl groups having 1 to 8 carbon atoms, alkoxyl groups having 1 to 8 carbon atoms, alkenyl groups having 2 to 8 carbon atoms or alkenyloxy groups having 3 to 8 carbon atoms, B represents a 1,4-phenylene group or trans-1,4-cyclohexylene group, and r represents 0 or 1), wherein the content of the compound represented by the general formula (Ib) is withing range of 5 to 50% by weight;

the content of the compound represented by the general formula (IIa) is within the range of 10 to 60% by weight; and the total content of the compounds represented by the general formulas (IIIa), (IIIb) and (IIIc) is within the range of 10 to 50% by weight.

11. A nematic liquid crystal composition containing one or more types of a compound having a 4,6-difluoroindan-2,5-diyl group; wherein, the substituent at the 5- of this compound is $-(Z^2-A^2)_m-R^2$ (wherein, $R^2$ represents a hydrogen atom, fluorine atom, chlorine atom, cyano group, trifluoromethyl group, fluoromethoxy group, difluoromethoxy group, trifluoromethoxy group, 2,2,2-trifluoroethyl group, alkyl group having 1 to 15 carbon atoms, alkenyl group having 2 to 15 carbon atoms or a hydrogen atom, said alkyl group or alkenyl group may be non-substituted or have one or more fluorine atoms, chlorine atoms, methyl groups or trifluoromethyl groups as substituents, and one or more methylene groups present in said alkyl group or alkenyl group may be substituted with —CO— or may be substituted with —S—, —O—, —OCOO—, —OCO— or —COO— in which the oxygen atoms are not mutually and directly bonded;

$A^2$ represents a group selected from the group consisting of:
(a1) a trans-1,4-cyclohexylene group (wherein one methylene group or two or more non-adjacent methylene groups present in this group may be substituted with —O— or —S—),
(b1) a 1,4-phenylene group (wherein one —CH= or two non-adjacent —CH= present in this group may be substituted with a nitrogen atom), and
(c1) a 1,4-cyclohexenylene group, 1,4-bicyclo(2.2.2) octylene group, piperidin-1,4-diyl group, naphthalen-2,6-diyl group, decahydronaphthalen-2,6-diyl group and 1,2,3,4-tetrahydro-naphthalen-2,6-diyl group, and the groups of (a1), (b1) or (c1) may each be substituted with a cyano group, fluorine atom or chlorine atom;

m represents 1 or 2;

$Z^2$ represents a group selected from the group consisting of —COO—, —OCO—, —CH$_2$O—, —OCH$_2$—, —CH$_2$CH$_2$—, —CH=CH—, —C≡C—, —(CH$_2$)$_4$—, —CH=CH—CH$_2$CH$_2$—, —CH$_2$CH$_2$—CH=CH— and a single bond;

in the case a plurality of $A^2$ and $Z^2$ are present, they may be the same or different;

the refractive index anisotropy is within the range of 0.08 to 0.15;

the liquid crystal phase upper limit temperature is 70° C. or higher;

the liquid crystal phase lower limit temperature is −20° C. or lower; and the difference between the liquid crystal phase upper limit temperature and liquid crystal phase lower limit temperature is 90° C. or more.

12. The nematic liquid crystal composition according to claim 11 wherein the compound having a 4,6-difluoroindan-2,5-diyl group is a compound represented by general formula (I):

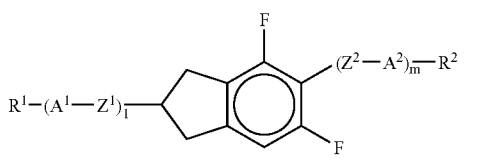

(wherein, $R^1$ represents an alkyl group having 1 to 15 carbon atoms, an alkenyl group having 2 to 15 carbon atoms, or a hydrogen atom, said alkyl group or alkenyl group may be non-substituted or have one or more fluorine atoms, chlorine atoms, methyl groups or trifluoromethyl groups as substituents, one or more methylene groups present in said alkyl group or alkenyl group may be substituted with —CO— or may be substituted with —S—, —O—, —OCOO—, —OCO— or —COO— in which the oxygen atoms are not mutually and directly bonded;

$A^1$ and $A^2$ respectively and independently represent a group selected from the group consisting of:
(a1) a trans-1,4-cyclohexylene group (wherein one methylene group or two or more non-adjacent methylene groups present in this group may be substituted with —O— or —S—),
(b1) a 1,4-phenylene group (wherein one —CH= or two non-adjacent —CH= present in this group may be substituted with a nitrogen atom), and
(c1) a 1,4-cyclohexenylene group, 1,4-bicyclo(2.2.2) octylene group, piperidin-1,4-diyl group, naphthalen-2,6-diyl group, decahydronaphthalen-2,6-diyl group and 1,2,3,4-tetrahydronaphthalen-2,6-diyl group, and the groups of (a1), (b1) or (c1) may each be substituted with a cyano group, fluorine atom or chlorine atom;

l represents 0, 1 or 2, m represents 1 or 2, and the sum of l and m is 2 or less;

$Z^1$ and $Z^2$ respectively and independently represent a group selected from the group consisting of —COO—, —OCO—, —CH$_2$O—, —OCH$_2$—, —CH$_2$CH$_2$—, —CH=CH—, —C≡C—, —(CH$_2$)$_4$—, —CH=CH—CH$_2$CH$_2$—, —CH$_2$CH$_2$—CH=CH— and a single bond;

$R^2$ represents a hydrogen atom, fluorine atom, chlorine atom, cyano group, trifluoromethyl group, fluoromethoxy group, difluoromethoxy group, trifluoromethoxy group, 2,2,2-trifluoroethyl group, alkyl group having 1 to 15 carbon atoms, alkenyl group having 2 to 15 carbon atoms or a hydrogen atom, said alkyl group or alkenyl group may be non-substituted or have one or more fluorine atoms, chlorine atoms, methyl groups or trifluoromethyl groups as substituents, and one or more methylene groups present in said alkyl group or alkenyl group may be substituted with —CO— or may be substituted with —S—, —O—, —OCOO—, —OCO— or —COO— in which the oxygen atoms are not mutually and directly bonded; and, in the case a plurality of $A^1$, $A^2$, $Z^1$ and $Z^2$ are present, they may be the same or different).

13. The nematic liquid crystal composition according to claim 11 or 12, or, further containing at least one type of compound represented by general formula (II):

$$R^3-B^1-L^1-B^2-(L^2-B^3)_o-R^4 \quad (II)$$

(wherein, $R^3$ and $R^4$ respectively and independently represent an alkyl group having 1 to 15 carbon atoms, an alkenyl group having 2 to 15 carbon atoms, or a hydrogen atom, said alkyl group or alkenyl group may be non-substituted or have one or more fluorine atoms, chlorine atoms, methyl groups or trifluoromethyl groups as substituents, one or more methylene groups present in said alkyl group or alkenyl group may be substituted with —CO— or may be substituted with —S—, —O—, —OCOO—, —OCO— or —COO— in which the oxygen atoms are not mutually and directly bonded;

$B^1$, $B^2$ and $B^3$ respectively and independently represent a group selected from the group consisting of:
(a1) a trans-1,4-cyclohexylene group (wherein one methylene group or two or more non-adjacent methylene groups present in this group may be substituted with —O— or —S—),
(b1) a 1,4-phenylene group (wherein one —CH= or two non-adjacent —CH= present in this group may be substituted with a nitrogen atom), and
(c1) a 1,4-cyclohexenylene group, 1,4-bicyclo(2.2.2) octylene group, piperidin-1,4-diyl group, naphthalen-2,6-diyl group, decahydronaphthalen-2,6-diyl group and 1,2,3,4-tetrahydronaphthalen-2,6-diyl group, and the groups of (a1), (b1) or (c1) may each be substituted with a cyano group, fluorine atom or chlorine atom;

o represents 0, 1 or 2; and, $L^1$ and $L^2$ respectively and independently represent a single bond, —CH$_2$CH$_2$—, —(CH$_2$)$_4$—, —OCH$_2$—, —CH$_2$O—, —CH=CH— or —C≡C—, and in the case a plurality of $L^2$ and $B^3$ are present, they may be the same or different).

14. The nematic liquid crystal composition according to claim 11 or 12, further containing one or more types of a compound selected from the group consisting of the compounds represented by general formulas (IIIa), (IIIb) and (IIIc):

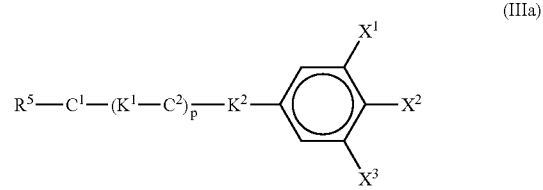

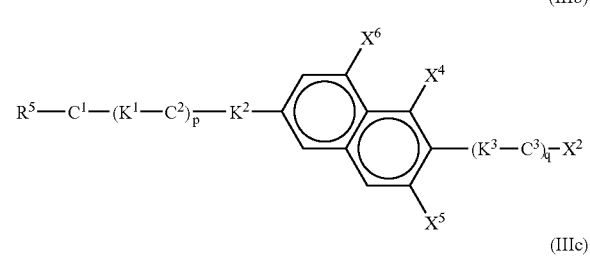

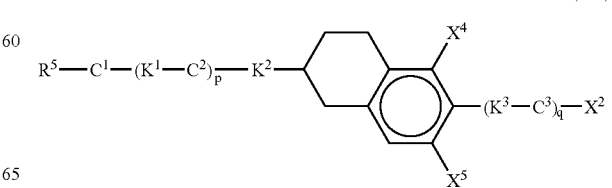

(wherein, $R^5$ represents an alkyl group having 1 to 15 carbon atoms, an alkenyl group having 2 to 15 carbon atoms, or a hydrogen atom in general formula (I), said alkyl group or alkenyl group may be non-substituted or have one or more fluorine atoms, chlorine atoms, methyl groups or trifluoromethyl groups as substituents, one or more methylene groups present in said alkyl group or alkenyl group may be substituted with —CO— or may be substituted with —S—, —O—, —OCOO—, —OCO— or —COO— in which the oxygen atoms are not mutually and directly bonded;

$C^1$, $C^2$ and $C^3$ respectively and independently represent a group selected from the group consisting of:
(d1) a trans-1,4-cyclohexylene group (wherein one methylene group or two or more non-adjacent methylene groups present in this group may be substituted with —O— or —S—),
(e1) a 1,4-phenylene group (wherein one —CH= or two non-adjacent —CH= present in this group may be substituted with a nitrogen atom), and
(f1) a 1,4-cyclohexenylene group, 1,4-bicyclo(2.2.2) octylene group, piperidin-1,4-diyl group, naphthalen-2,6-diyl group, 1,2,3,4-tetrahydronaphthalen-2,6-diyl group and decahydronaphthalen-2,6-diyl group, and the groups of (d1), (e1) or (f1) may each be substituted with a cyano group, fluorine atom or chlorine atom;

$K^1$, $K^2$ and $K^3$ respectively and independently represent a single bond, —$CH_2CH_2$—, —$(CH_2)_4$—, —$OCH_2$—, —$CH_2O$—, —COO—, —OCO— or —C≡C—;

$X^1$, $X^3$, $X^4$, $X^5$ and $X^6$ respectively and independently represent a hydrogen atom or fluorine atom;

p and q respectively and independently represent 0, 1 or 2, and the sum of p and q is 2 or less; and, $X^2$ represents a hydrogen atom, fluorine atom, chlorine atom, cyano group, trifluoromethyl group, fluoromethoxy group, difluoromethoxy group, trifluoromethoxy group, 2,2,2-trifluoroethyl group, alkyl group having 1 to 15 carbon atoms, alkenyl group having 2 to 15 carbon atoms or a hydrogen atom, said alkyl group or alkenyl group may be non-substituted or have one or more fluorine atoms, chlorine atoms, methyl groups or trifluoromethyl groups as substituents, and one or more methylene groups present in said alkyl group or alkenyl group may be substituted with —CO— or may be substituted with —S—, —O—, —OCOO—, —OCO— or —COO— in which the oxygen atoms are not mutually and directly bonded).

15. The nematic liquid crystal composition according to claim 14 wherein the sum of the contents of the compounds that compose the group consisting of compounds represented by general formulas (IIIa), (IIIb) and (IIIc) is within the range of 10 to 50% by weight.

16. The nematic liquid crystal composition according to claim 13 containing a compound represented by general formula (IIa):

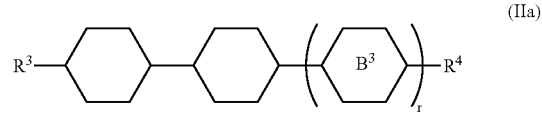

(IIa)

(wherein, $R^3$ and $R^4$ represent alkyl groups or alkoxy groups having 1 to 8 carbon atoms, alkenyl groups having 2 to 8 carbon atoms or alkenyloxy groups having 3 to 8 carbon atoms, $B^3$ represents a 1,4-phenylene group or trans-1,4-cyclohexylene group, and r represents 0 or 1).

17. The nematic liquid crystal composition according to claim 16 wherein the content of the compound represented by general formula (IIa) is within the range of 10 to 80% by weight.

18. A liquid crystal display element that uses the nematic liquid crystal composition according to claim 1.

19. An active matrix liquid crystal display element that uses the nematic liquid crystal composition according to claim 1.

20. A compound represented by general formula (Ib):

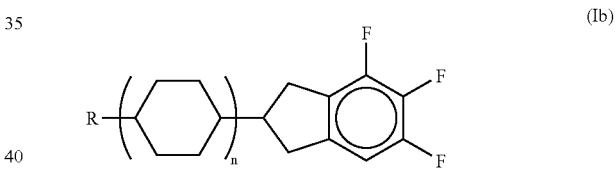

(Ib)

(wherein, R represents an alkyl group having 1 to 12 carbon atoms or an alkenyl group having 2 to 12 carbon atoms, and n represents 1 or 2).

* * * * *